(12) United States Patent
Raghukumar et al.

(10) Patent No.: US 6,395,534 B1
(45) Date of Patent: May 28, 2002

(54) **WHITE ROT-LIGNIN-MODIFYING FUNGUS *FLAVODON FLAVUS* AND A PROCESS FOR REMOVING DYE FROM DYE CONTAINING WATER OR SOIL USING THE FUNGUS**

(75) Inventors: Chandralata Raghukumar, Goa (IN); Trevor M. D'Souza, East Lansing, MI (US); R. Greg Thorn, Laramie, WY (US); C. A. Reddy, East Lansing, MI (US)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/456,559

(22) Filed: Dec. 8, 1999

(30) Foreign Application Priority Data

Mar. 31, 1999 (IN) ......................... 494/DEL/99

(51) Int. Cl.[7] ................................. C12N 1/18
(52) U.S. Cl. ..................... 435/254.1; 435/911
(58) Field of Search ............... 435/254.1, 911

(56) References Cited

U.S. PATENT DOCUMENTS

| | | | | |
|---|---|---|---|---|
| 5,091,089 A | 2/1992 | Shen et al. | ................. | 210/611 |
| 5,755,514 A | 5/1998 | Baar-Bartelt | ................ | 383/104 |

FOREIGN PATENT DOCUMENTS

| | | | | |
|---|---|---|---|---|
| DE | 290 004 | 12/1989 | ...................... | 3/34 |
| JP | 6-47394 | 2/1994 | ...................... | 3/32 |

OTHER PUBLICATIONS

Rattan et al., J. Res. (Punjab Agric. Univ.), (1983 (RECD 1984) 20 (2), 228–229.*

Purkayastha, et al., Proceedings of the Indian National Science Academy Part B Biological Sciences, (1994) vol. 60, No. 3, pp. 269–275.*

Bumpus, et al., Biedegradation of Crystal Violet by the While Rot Fungus, Applied and Environmental Microbiology, May 1988, vol. 54, No. 5, pp. 1143–1150.

Raghukumar, et al., Lignin–Modifying Enzymes of Flavodon Flavus, a Basidiomycete Isolated from a Coastal Marine Environmental, Applied and Environmental Microbiology, May 1999, vol. 65, No. 5, pp. 2103–2111.

Reddy, The Potential for While–Rot Fungi in the Treatment of Pollutants, Environmental Biotechnology, 1995, vol. 6, pp. 320–328.

Heinfling, et al., Biodegradation of AZO and Phthalocyanine Dyes by Trametes Versicolot and Bjerkandera Adusta; appl. Microbiol. Biotechnol. 1997, vol. 48, pp. 261–266.

Gold, et al., Use o Polymeric Dyes in Lignin Biodegradation Assays, Methods in Enzymology, 1978, vol. 161, pp. 74–78.

Paszczynshi, et al., Manganese Peroxidase of Phanerochaete Chrysosporium: Purification, Methods in Enzymology, vol. 161, pp. 264–270.

Tien, et al., Lignin Peroxidase of Phanerochaete Chrysosporium; Methods in Enzymology, vol. 161, pp. 238–249.

Niku–Paavola, et al., Ligninolytic Encymes of the Ehite–Rot Fungus Phlebia Radiata, Biochem. J. 1988, vol. 254, pp. 877–884.

Michel, et al., Role of Manganese Peroxidases and Lignin Peroxidases of Phanerochaete Chrysosporium in the Decolorization of Kraft Bleach Plant Effluent, Applied and Environmental Microbiology, Aug. 1991, vol. 57, No. 8 pp. 2368–2375.

\* cited by examiner

*Primary Examiner*—Irene Marx
(74) *Attorney, Agent, or Firm*—Smith, Gambrell & Russell, LLP

(57) ABSTRACT

The invention relates to a biologically pure culture of white rot lignin-modifying fungus *Flavodon flavus* for simultaneous decolorization and detoxification of molasses spent wash or water/soil contaminated with molasses spent wash. The *Flavodon flavus* has been deposited at the National Institute of Oceanography, Goa, India, bearing Accession No. NIOCC #312 and has also been deposited at Agricultural Research Service Culture Collection (NRRL), 1815 North University Street, Peoria, Ill. 61604, U.S.A., bearing Accession No. NRRL 30302 on Mar. 10, 2000.

1 Claim, 19 Drawing Sheets

Low nitrogen medium with half-strength artificial sea water
Congo red

Low nitrogen medium with half-strength artificial sea water
Poly-B

Low nitrogen medium with half-strength artificial sea water
Poly-R

Azure B

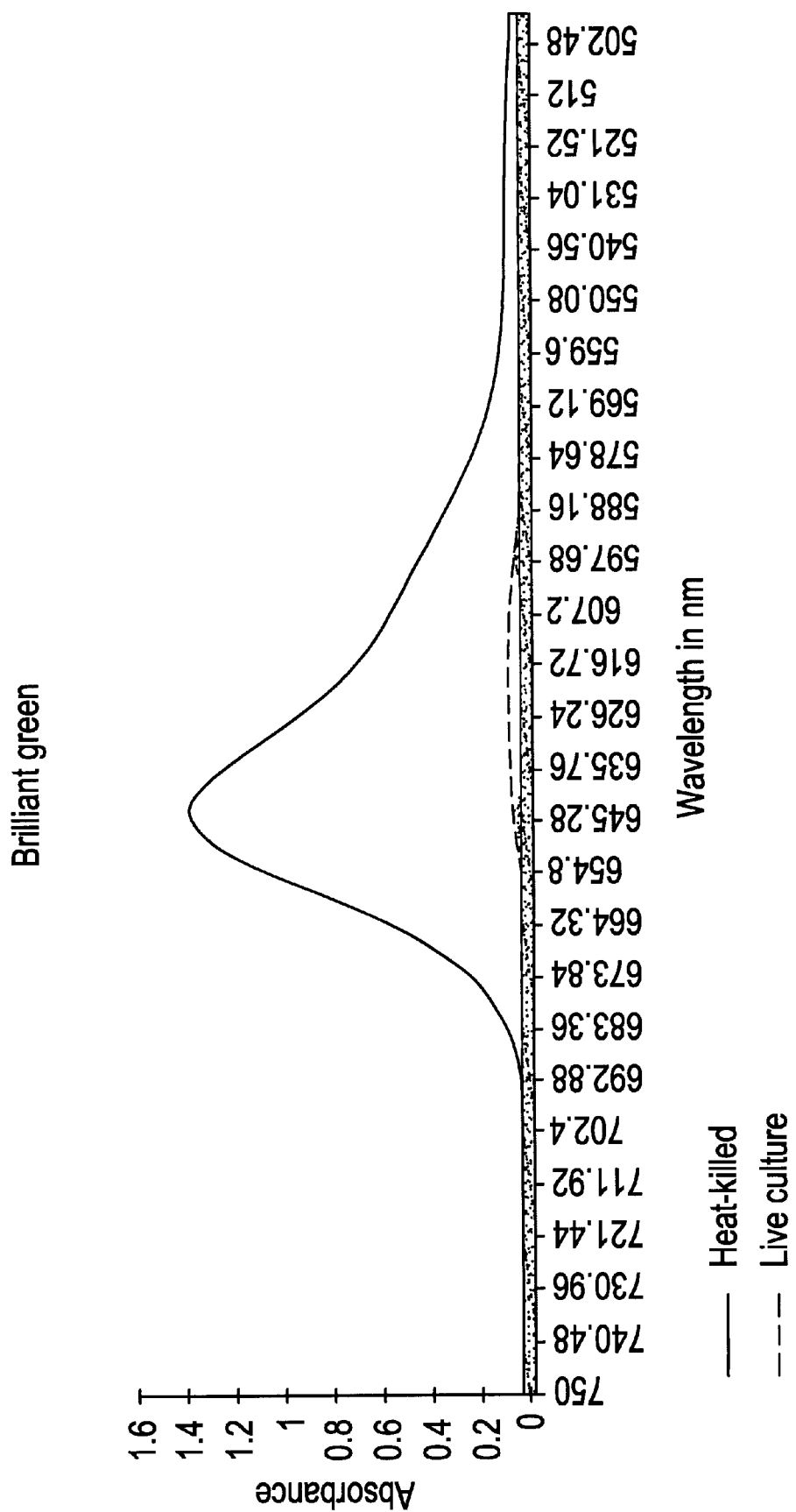

Congo Red

MNP production in malt extract broth

LIP production in malt extract broth

Laccase production in malt extract broth

MNP in low nitrogen medium prepared with half-strength artificial sea water

Laccase in low nitrogen medium prepared with half-strength artificial sea water

MNP production in sugarcane bagasse suspended in distilled water

LIP production in sugarcane bagasse suspended in distilled water

Laccase production in sugarcane bagasse suspended in distilled water

MNP production in sugarcane bagasse suspended in half-strength artificial sea water Laccase production in sugarcane bagasse suspended in half-strength artificial sea water

WHITE ROT-LIGNIN-MODIFYING FUNGUS *FLAVODON FLAVUS* AND A PROCESS FOR REMOVING DYE FROM DYE CONTAINING WATER OR SOIL USING THE FUNGUS

FIELD OF THE INVENTION

This invention relates to a lignin-modifying white-rot fungus, *Flavodon flavus* (K1) Ryv., deposited at National Institute of Oceanography, Dona Paula, Goa, India, at accession No. NIOCC #312, and a process for removal of dyes in dye containing waste-waters and soil. The present invention particularly relates to a process for removal of synthetic dyes in dye containing waste-waters and the soil using lignin-modifying white-rot fungus, *Flavodon flavus* (K1) Ryv., NIOCC isolate 312. The lignin-modify white-rot fungus, *Flavodon flavus* (K1) Ryv. was also deposited at Agricultural Research Service Culture Collection (NRRL), 1815 North University Street, Peoria, Ill. 61604, U.S.A., bearing accession No. NRRL 30302 on Mar. 10, 2000.

BACKGROUND OF THE INVENTION

Textile and dyestuff industries are the major contributors to industrial pollutants containing dyes. These dyes are highly stable in light and are also resistant to microbial attack. Most of these dyes are azo dyes and under anaerobic conditions, the azo linkages are reduced to form aromatic amines and these are toxic and carcinogenic (Meyer, U. 1981. Biodegradation of synthetic organic colorants. Federation of European Microbiological Societies Symposium. 12: 371–385). Due to the importance attached to prevention of environmental pollution, environmental agencies all over the world are imposing strict regulations for mitigation of pollution from industries. The effluents from the textile industries containing fast colored dyes are a major source of concern for environmentalists since such dyes besides causing aesthetic damage to sites, are toxic and carcinogenic. Industrial effluents from textiles, paper and pulp industries and leather industries contain chromogenic substances as well as high concentrations of salts, especially chlorides and sulfates (Public Health Engineering-Design in Metric wastewater treatment by R. E. Bartlett, 1971, Applied Science Publishers Ltd., London). Remediation of such dye containing waste-waters using biological methods is termed bioremediation.

Normally, the textile dye waste-waters disposal includes physical-chemical treatment, waste minimization and biological treatment. Biological treatment includes biological pretreatment with activated sludge of textile waste-waters, and treatment in stabilization ponds (Groff, K. A. 1992, Textile waste. Water-Environment Research, 64: 725–729.). Unfortunately, waste-water treatment facilities are often unable to completely remove commercial dyestuff from contaminated waters and thus contribute to pollution of aquatic habitats. Some of these synthetic dyes are carcinogenic and are suggested to be responsible for tumor growth in some species of fish (see Bumpus J. A., B. J. Brock. 1988. Biodegradation of crystal violet by the white-rot fungus *Phanerochaete chrysosporium*. Applied and Environmental Microbiology, 54:1143–1150).

Various organisms have been tried for degradation of dyes in textile waste-waters and bioremediation.

(i) Reference is made to the Japanese patent JP 06047394 Titled: Organic dye degradation in waste-water, issued on: 22.02.94, wherein a green alga *Chlorella vulgaris* is used for degradation of methylene blue by irradiating a microalga fermentor to generate OH radicals which in turn help in degradation of the dye. The method has a disadvantage as it involves irradiating the fermentor containing microalga and thus becomes expensive.

(ii) Reference may be made to U.S. Pat. No. 5,091,089 dated Feb. 25, 1992 Title: Decolorization of dye-containing waste-water, wherein, living, dead, free, immobilized white-rot fungi Myrothecium or Ganoderma sp. have been employed for adsorption, dye degradation and color removal. These fungi have not been tested for their efficiency in color removal in the presence of sea salts.

(iii) Reference may be made to U.S. Pat. No. 5,755,514 dated Mar. 24, 1992 Title: Increasing biodegradability of xenobiotic azo dyes wherein, white-rot fungus *Phanerochaete chrysosporium* and actinomycetes Streptomyces spp are used in degradation of xenobiotic azo dyes. They are not shown to degrade azo dyes in the presence of sea salts.

(vi) Reference may be made to a publication wherein *Phanerochaete chrysosporium* is reported to degrade textile azo dyes very efficiently under conditions where lignin-modifying enzymes are produced by incubating cultures at 39° C., (Capalash, M. and P. Sharma. 1992. Biodegradation of textile azo-dyes by *Phanerochaete chrysosporium*. World Journal of Microbiology and Biotechnology. 8:309–312). However, it has not been shown to degrade synthetic dyes in the presence of sea salts. The fungal culture needs to be incubated at 39° C. for effective degradation, which may involve additional step during treatment of wastewater.

(v) A reference may be made to German patent (DD-290004, entitled 'Microbial breakdown of xenobiotic dyes of triphenylmethane series', issued on May. 16, 1991) wherein, degradation of crystal violet and malachite green are brought about by oleophilic Gram-positive bacteria preferably Corynebacterium sp. IMET 11347 or Mycobacterium sp.

IMET 11349. The disadvantage of this system is that the organisms have to be grown at 32° C. in 1% methanol and removal of bacterial inoculum from dye-containing waste-water will not be very easy.

The fungus *Flavodon flavus* belonging to the class Basidiomycetes produces fertile basidiomata in medium containing alpha-cellulose and sometimes in malt extract agar medium on prolonged incubation. Most of the times the fungus is in non-sprouting form and can be recognized by crystals deposited around fungal hyphae.

Many lignin-degrading fungi can also degrade textile azo dyes but their growth and enzyme production in presence of synthetic sea water has not been demonstrated. The applicants have used a strain of *Phanerochaete chrysosporium* and observed that it does not grow in synthetic sea water. This implies that it cannot effect dye degradation in the presence of sea water either. Caplash et al., 1992 have also used a strain of *Phanerochaete chrysosporium* in their studies.

Although presence of lignin-modifying enzymes are reported in several fungal taxa belonging to the class Basidiomycetes, the applicants reported their presence in *Flavodon flavus* for the first time (Raghukumar, C., T. M. D'Souza, R. G. Thom and C. A. Reddy, 1999. Lignin-modifying enzymes of *Flavodon flavus*, a basidiomycete isolated from a coastal marine environment. Applied Environmental Microbiology 65:2103–2111). *Flavodon flavus*, NIOCC isolate #312 is a close relative of Irpex and the Polyporus-Trametes lineage of polypores (Ryvarden L. 1991. Genera of Polypores. Synopsis Fungorum 5, Fungiflora, Oslo, Norway). Cultural characteristics of the isolate #312 were studied in malt extract agar medium and on alphacel agar. Fertile basidiomata that occurred on this media were identified as *Flavodon flavus* on the basis of their smooth nonamyloid basidiospores, dimitic hyphal system with skeletal hyphae and simple septet generative hyphae, incrusted hymenal cystidia and poroid-hydnoid yellow fruiting bodies. Occurrence and taxonomy of this fungus is reported from Indian forests (Sen M. 1973. Cultural diagnosis of Indian Polyporaceae. 3. Genera Daedalea, Favolus, Ganoderma, Hexagonia, Irpex, Lenzites, Merulius, and Poria. Indian Forest Records (New Series) Forest Pathology, Vol. 2, No. 11, Dehra Dun, India). The applicants have isolated it from marine habitat for the first time. The applicants also shown that it grows much better in the presence of synthetic sea water. (The identification of this fungus was carried out by Dr. R. G. Thorn from Department of Botany, University of Wyoming, Laramie, WY 82071–3165, U.S.A., who is also a co-author in the above mentioned publication).

OBJECTS

The main objective of the present invention is to identify and provide novel white-rot fungus *Flavodon flavus* (K1) Ryv. Deposited at National Institute of Oceanography, (and at Agricultural Research Service Culture Collection (NRRL), 1815 North University Street, Peoria, Ill. 61604, U.S.A., bearing accession No. NRRL 30302), exhibiting lignin degrading properties.

Another object of the invention is to provide a process for removal of dyes using the lignin-modifying white-rot fungus, *Flavodon flavus*, for possible use in dye-containing waste-water and in saline soils. The said fungus can be efficiently utilized for the above-mentioned usage in fresh water as well as under estuarine conditions because of its tolerance to sea salts.

Yet another objective is to provide a process for cultivation of the novel fungus on a large scale using inexpensive raw material such as sugarcane bagasse suspended in distilled water or 50% artificial sea water or simple medium like malt extract broth prepared with fresh water as well as 50% artificial sea water.

DETAILED DESCRIPTION OF THE INVENTION

In accordance with the foregoing objects, the invention provides novel white-rot fungus *Flavodon flavus* deposited at National Institute of Oceanography, Dona Paula, Goa, India, at accession No. 312. The invention also provides a process for removal of dyes in dye-containing effluent waters and soil, which comprises the steps of growing the white rot fungus *Flavodon flavus* in a nutrient medium containing assimilable carbon and nitrogen source, having optimal salinity up to 15 parts per thousand for a period of about 4–10 days, contacting biomass with effluents containing dyes for a period of at least 5 days followed by separation of the fungal biomass from the effluents by conventional methods to render the effluents substantially free of dyes.

In an embodiment, the fungus *F. flavus* is capable of treating estuarine waters, fresh water, effluents selected from textile, leather and paper industries.

In another embodiment, the effluents may be waste-water containing dyes or soil containing dyes.

In an embodiment the nutrient medium used for growth of the fungus is selected from glucose, sugar-cane bagasse suspended in distilled water, synthetic media, low. nitrogen medium, malt extract broth prepared with fresh water and 50% sea water.

In another embodiment, the fungus *F. flavus* is grown in nutrient medium comprising malt extract broth containing about 2% malt extract and about 0.3% peptone in distilled water.

In yet another embodiment, synthetic media is prepared in distilled water or 50% artificial sea water containing 1% glucose as carbon source, 2.4 mM ammonium tarterte as nitrogen source, thiamin, trace metal solution, macro element solution containing potassium and manganese salts, Tween 80, veratryl alcohol and 20 mM sodium acetate buffer at pH 4.5.

In a further embodiment, the low nitrogen medium comprises 10 g glucose as the carbon source, 2.4 mm ammonium tartrate as the nitrogen source, 70 ml of trace metal solution from stock solution containing $MgSO_4$ 3 g, $MnSO_4$ 0.5 g, NaCl 1.0 g, $FeSO_4$ $7H_2O$ 0.1 g, $CoCl_2$ 0.1 g, $ZnSO_4$ $7H_2O$ 0.1 g, $CuSO_4$ 0.1 g, $AlK(SO_4)_2$ $12H_2O$ 10 mg, $H_3BO_3$ 10 mg, $Na_2MoO_4$ $2H_2O$ 10 mg, Nitrilotriacetate 1.5 g in 1 L distilled water, one hundred ml of macro element solution containing $KH_2PO_4$ 20 g, $MgSO_4$ 5 g, $CaCl_2$ 1 g in 1 L of distilled water, one percent Tween 80, 1 ml from 0.4 M stock solution of veratryl alcohol, 10 ml of thiamin from stock solution containing 100 mg in 1 L distilled water and 20 mm sodium acetate buffer.

In yet another embodiment, the pH of the nutrient medium is maintained at 4.5.

In a further embodiment, the salinity of the medium for growing the fungus is maintained at about 0 to 15 parts per thousand.

In yet another embodiment, the fungus is grown in the nutrient medium for a period of about 4–10 days.

In another embodiment, the fungal biomass is immobilized on a conventional support such as nylon mesh by conventional methods selected from immobilization and adsorption.

In yet another embodiment, the fungus is capable of degrading pollutants selected from the group of synthetic dyes comprising azo, heterocyclic and polymeric dyes.

In a further embodiment, the effluents are degraded by contacting with the effluents with fungal biomass.

In yet another embodiment, the fungal biomass is separated from the effluents manually or by filtration.

In an embodiment of the present invention, a process is provided for removal of synthetic dyes using the lignin-modifying white-rot fungus, *Flavodon flavus*, NIOCC 312 for possible use in dye-contaminating waste-waters and soil in the presence of salts. The said fungus may be efficiently utilized for the above-mentioned usage in fresh water as well as under estuarine conditions because of its tolerance to sea salts.

In another embodiment of the present invention, the fungus may be grown on large scale in an inexpensive raw material such as sugarcane bagasse suspended in distilled water or 50% artificial sea water or simple medium like malt extract broth prepared with fresh water or with 50% artificial sea water. The biomass of the fungus thus raised may be used for seeding dye-contaminated wastewater in a freshwater or estuarine environment or for seeding soil contaminated with synthetic dyes.

In yet another embodiment, the said fungus may be immobilized on a suitable substrate, and the immobilized fungus may be used for seeding the soil and aquatic habitats contaminated with synthetic dyes.

The organism given in the present invention is a white-rot basidiomycete fungus isolated from a decaying marine plant from a coastal marine environment and identified as *Flavodon flavus*. The said fungus *F. flavus* can be grown in malt extract broth containing 2% malt extract and 0.3% peptone in distilled water. The biomass of the fungus can be used for seeding soil contaminated with synthetic dyes for treating dye-containing waste water under normal conditions or under estuarine conditions. The biomass of the said fungus thus raised can also be immobilized using conventional methods used for immobilizing fungi and used for bioremediation of dye-containing aquatic systems.

The fungal mat is macerated using a homogeniser and used as starter inoculum for the experimental cultures of synthetic media prepared in distilled water or in 50% artificial seawater. The synthetic media can be prepared in distilled water or 50% artificial sea water containing 1% glucose as carbon source, 2.4 mM ammonium tartrate as the nitrogen source, thiamin, trace metal solution, macro element solution containing potassium and manganese salts, Tween 80, veratryl alcohol and 20 mM sodium acetate buffer at pH 4.5. This medium is referred to as low nitrogen medium. An example of the process for dye degradation involves addition of various synthetic dyes such as Azure B. Brilliant Green, Congo Red, Crystal Violet, Remazol Brilliant Blue R and polymeric dyes such as Poly B-411 and Poly R-478 at a final concentration of 0.02% to 3 day old cultures of *F. flavus* growing in malt extract broth, synthetic medium prepared with distilled water or 50% artificial sea water. The degradation of dyes can be monitored spectrophotometrically by removing an aliquot of sample from these cultures and measuring changes in absorbance at respective wavelengths of various dyes every alternate day up to 10 days. Heat-killed cultures serve as controls where no decolorization or degradation of dyes is observed. Moreover, the said fungus can be grown on a large scale using an inexpensive raw material such as sugarcane bagasse suspended in distilled water or in 50% artificial sea water. The said fungus produces lignin-modifying enzymes such as manganese-dependent peroxidase (MNP), lignin peroxidase (LIP) and laccase, in conventional media prepared with distilled water as well as in media prepared with 50% artificial sea water.

The fungus can be grown in the medium generally referred to as low nitrogen medium (Tien M. and T. K. Kirk, 1988. Lignin peroxidase of *Phanerochaete chrysosporium*. Methods in Enzymology 161: 238–249). The low nitrogen medium contains 10 g glucose as the carbon source, 2.4 mm ammonium tartrate as the nitrogen source, 70 ml of trace metal solution from stock solution containing $MgSO_4$ 3 g, $MnSO_4$ 0.5 g, NaCl 1.0 g, $FeSO_4$ $7H_2O$ 0.1 g, $CoCl_2$ 0.1 g, $ZnSO_4$ $7H_2O$ 0.1 g, $CuSO_4$ 0.1 g, $AlK(SO_4)$, $12H_2O$ 10 mg, $H_3Bo_3$ 10 mg, $Na_2MoO_4$ $2H_2O$ 10 mg, Nitrilotriacetate 1.5 g in 1 L distilled water. One hundred ml of macro element solution containing $KH_2PO_4$ 20 g, $MgSO_4$ 5 g, $CaCl_2$ 1 g in 1 L of distilled water. One percent Tween 80, 1 ml from 0.4 M stock solution of veratryl alcohol, 10 ml of thiamin from stock solution containing 100 mg in 1 L distilled water and 20 mm sodium acetate buffer to maintain pH at 4.5. the culture needs to be flushed with pure oxygen every third day as it is known that lignin-degrading enzyme system works well under conditions of oxygen saturation.

Low nitrogen medium prepared with half strength synthetic seawater for growing this fungus has been reported for the first time by the applicants. This modification of low nitrogen medium of Tien and Kirk (1988) was optimized by the applicants.

Cultural characters of #312 were studied in malt extract agar medium (MEA) containing 1.25% malt extract and 2% agar (Nobles, 1948). The culture code provided for #312 is that of (Nobles, 1965; Ginns and Lefebvre, 1993); 2a.6.8.13.32.36.40.43.48.50.54, where code 2a represents detection of laccase with a positive syringaldazine spot-test and peroxidase as detected by application of 0.4% $H_2O_2$ to a syringaldazine spot-test (Harkin and Obst, 1973 . Growth fast, plates covered in 2–3 weeks (code 42–43); margin even, appressed, fimbriate to wispy, hyaline, aerial mycelium sparse to moderate after 2 weeks, low and thin, downy with cottony patches, hyaline to white; after 6 weeks mostly cottony, white to cream with sulfur yellow patches; reverse of the plates bleached (code 40); not fruiting within 6 weeks (code 48); odour nil to faintly resiny-fragrant (code 50); marginal hyphae tubular, straight, thin-walled, 2.5–4.0 $\mu$m diam, with simple septa, sparsely branched, mostly from immediately behind septa; dolipore septa visible with ammoniacal congo red; cultures monomitic but in age with scattered, encrusted cystidia resembling skeletal hyphae; lacking any form of conidia or noteworthy hyphal swellings.

Several very old subcultures fruited on MEA and alpha-cellulose agar producing identifiable basidiomata. Basidiomata pulvinate, 2–5 mm broad, sulphur yellow, irregularly poroid-toothy; pores approximately circular, 1–2 per mm, lined with a hymenium of 4-spored, clavate basidia (24–28× 6–8 $\mu$m) and fusoid-cylindric, thick walled cystidia (28–38× 3.5–5.0 $\mu$m). The hyphal system was dimitic with simple septate generative hyphae 2.0–3.5 $\mu$m in diam and infrequently branched, tubular skeletal hyphae 2.0–5.0 $\mu$m in diam. Skeletal hyphae terminated in the hymenium as cylindrical, thick-walled pseudocystidia. Basidiospores hyaline, nonamyloid, smooth, thin-walled, elliptical to lacrymoid, 6.0–7.0×3.0–3.8 $\mu$m. Fruiting bodies from culture were identified as *Flavodon flavus* (Klotzsch) Ryvarden using the keys in Ryvarden and Johansen (1980).

Lack of salt tolerance in most ectomycorrhizal basidiomycetes was reported by Hutchinson (1990) and in wood-inhabiting corticoid fungi by Thorn (1991). Tolerance to synthetic sea salt as shown by growth, production of lignin-modifying enzymes and dye decolorization in this trail of *F. flavus* was reported for the first time by the applicants (Raghukumar et al., 1999).

The said fungus *Flavodon flavus*, NIOCC isolate 312, is capable of growing in the presence of salts whose concentration is similar to that found in half-strength sea water. Most of the industrial effluents from textiles, dyestuff, paper and pulp and leather industries contain chromogenic substances as well as high concentrations of salts, especially chlorides and sulfates (Public Health Engineering—Design in Metric waste-water treatment by R. E. Bartlett, 1971, Applied Science Publishers Ltd., London). In light of this, salt tolerant organisms are better suited for such waste-water treatments.: Most of the fungi used for bioremediation of such colored waste-waters have not been tested for their salt tolerance. In view of this, the present process has an advantage over the conventional processes referred to in various patents discussed above. White-rot fungi are unique among eukaryotic microbes in possessing powerful lignin-degrading oxidative enzymes such as MNP, LIP and lacasses, which have a broad substrate specificity and are thus able to oxidize several environmental pollutants. Results from several laboratories have shown that the ability of white-rot fungi such as *Phanerochaete chrysosporium* and Trametes versicolor to degrade an array of pollutants including synthetic dyes such as axo, heterocyclic and polycyclic dyes is due to the lignin-modifying/degrading system (C A. Reddy. 1995. The potential for white-rot fungi in the treatment of pollutants. Current Opinion in Biotechnology, 6: 320–328). The fungal isolate *F. flavus*, NIOCC isolate 312, obtained from marine environment also produces lignin-modifying enzymes such as MNP LIP and laccase. It produces these enzymes in natural media such as ME broth, conventional synthetic medium prepared with distilled water or 50% artificial sea water and also in powdered sugarcane bagasse suspended in distilled water or in 50% artificial sea water, and degrades synthetic dyes such as Azure B, Brilliant Green, Crystal Violet, Congo Red, Remazol Brilliant Blue R and polymeric dyes such as Poly B and Poly R.

Thus, this invention particularly relates to degradation of synthetic dyes in the presence of salts by the fungus *F. flavus* deposited at the National Institute of Oceanography, Dona Paula, Goa 400004, India, having accession number NIOCC 312, in textile waste-water treatment, and bioremediation of soil. The said fungus can also be grown in conventional media or in powdered sugarcane bagasse suspended in distilled water or 50% artificial sea water to raise large biomass of the fungus for application in field trials for bioremediation in the presence of sea water or fresh water. The said fungus thus grown can be immobilized by conventional methods and used for removal of various synthetic dyes from contaminated soil as well as aquatic habitats. The said fungus, *F. flavus* produces lignin-modifying enzymes such as manganese-dependent peroxidase E. C. 1.11.1.7 (NNP), lignin peroxidase, E. C. 1.11.1.7 (LIP) and laccase, E. C. 1.10.3.2 when grown on sugarcane bagasse suspended in plain distilled water or in 50% artificial sea water or in conventional media prepared with distilled water or 50% artificial sea water. By virtue of these lignin-modifying enzymes which break down a broad range of polymeric substrates, this fungus is useful in degradation of pollutants such as synthetic dyes. Thus degradation of synthetic dyes in waste-waters can be achieved by using the fungus *F. flavus* in fresh water as well as estuarine conditions.

BRIEF DESCRIPTION OF THE DRAWINGS

The invention is further illustrated in greater detail with reference to the accompanying drawings wherein:

FIG. 4b. depicts spectrum of undegraded Brilliant green in control heat-killed culture and the same after degradation in live culture of the isolate #312.

Figure 1A:
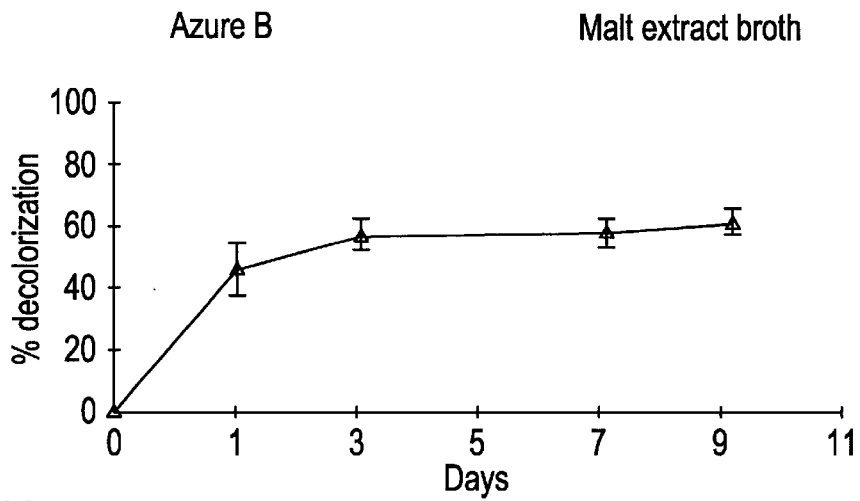
FIG. 1a. represents decolorization of Azure-B by the fungus *Flavodon flavus*, NIOCC isolate #312, grown in the malt extract broth. The results are given as the difference in percent decolorization between heat-killed control and the experimental live cultures.
Figure 1B:
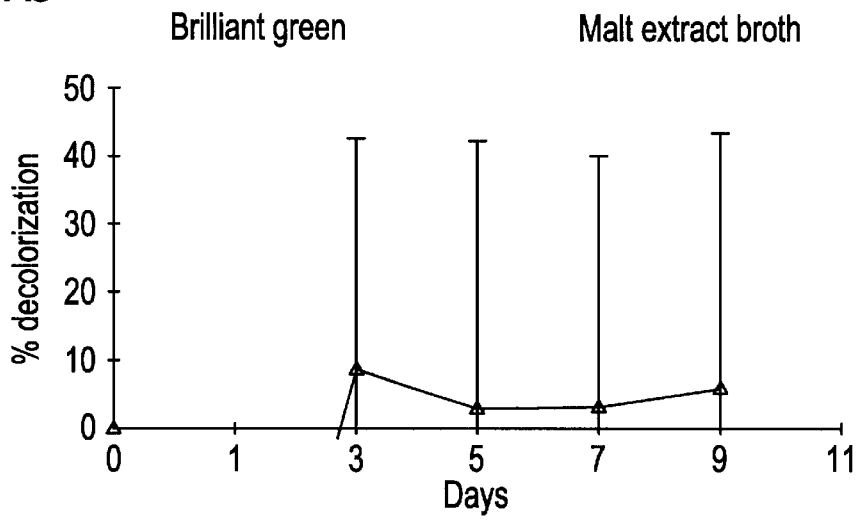
FIG. 1b. depicts decolorization of Brilliant green by the fungus *Flavodon flavus*, NIOCC isolate #312, grown in the malt extract broth. The results are given as the difference in percent decolorization between heat-killed control and the experimental live cultures.
Figure 1C:
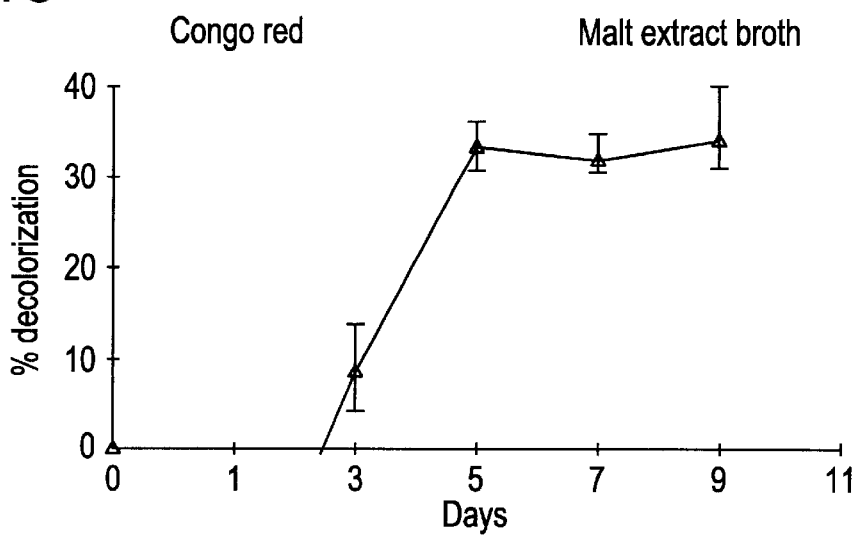
FIG. 1c. depicts decolorization of Congo red by the fungus *Flavodon flavus*, NIOCC isolate #312, grown in the malt extract broth. The results are given as the difference in percent decolorization between heat-killed control and the experimental live cultures.
Figure 1D:
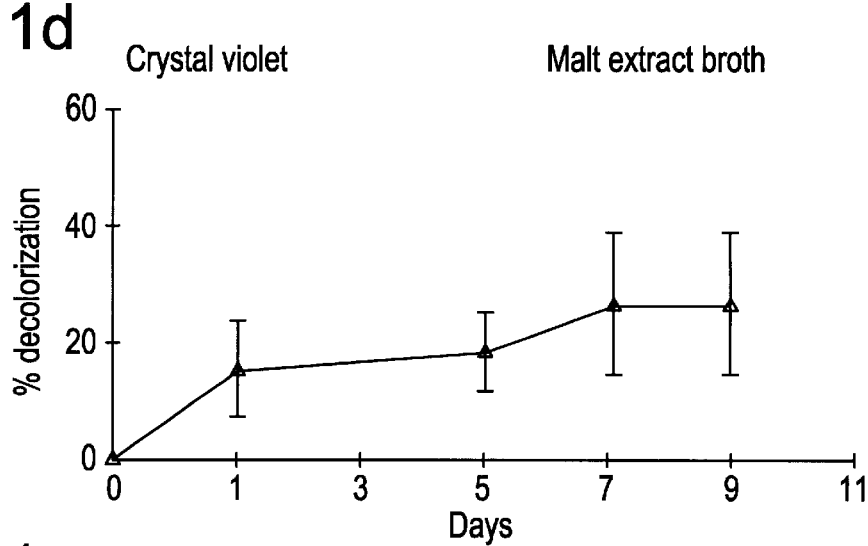
FIG. 1d. depicts decolorization of Crystal violet by the fungus *Flavodon flavus*, NIOCC isolate #312, grown in the malt extract broth. The results are given as the difference in percent decolorization between heat-killed control and the experimental live cultures.
Figure 1E:
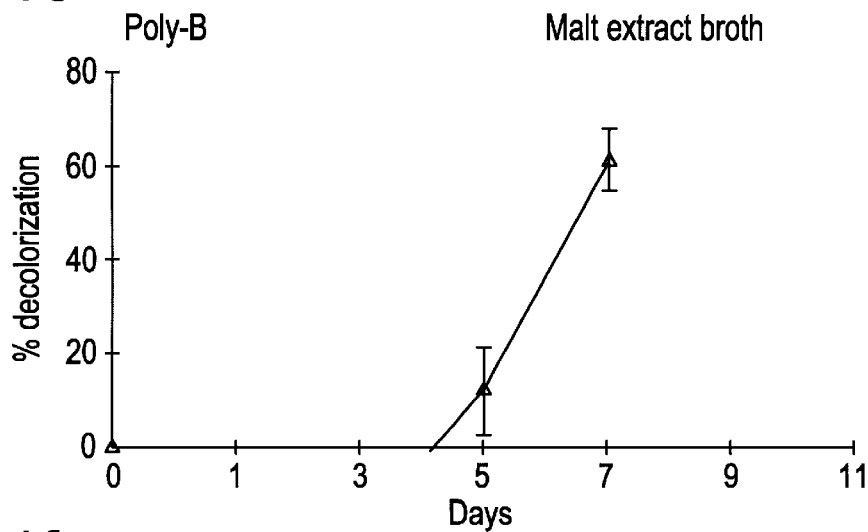
FIG. 1e. depicts decolorization of Poly-B by the fungus *Flavodon flavus*, NIOCC isolate #312, grown in the malt extract broth. The results are given as the difference in percent decolorization between heat-killed control and the experimental live cultures.
Figure 1F:
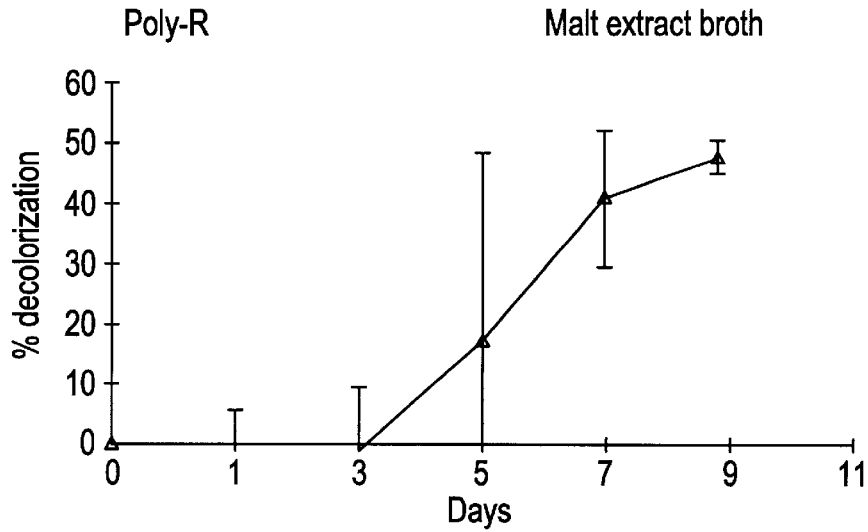
FIG. 1f. depicts decolorization of Poly-R by the fungus *Flavodon flavus*, NIOCC isolate #312, grown in the malt extract broth. The results are given as the difference in percent decolorization between heat-killed control and the experimental live cultures.
Figure 1G:
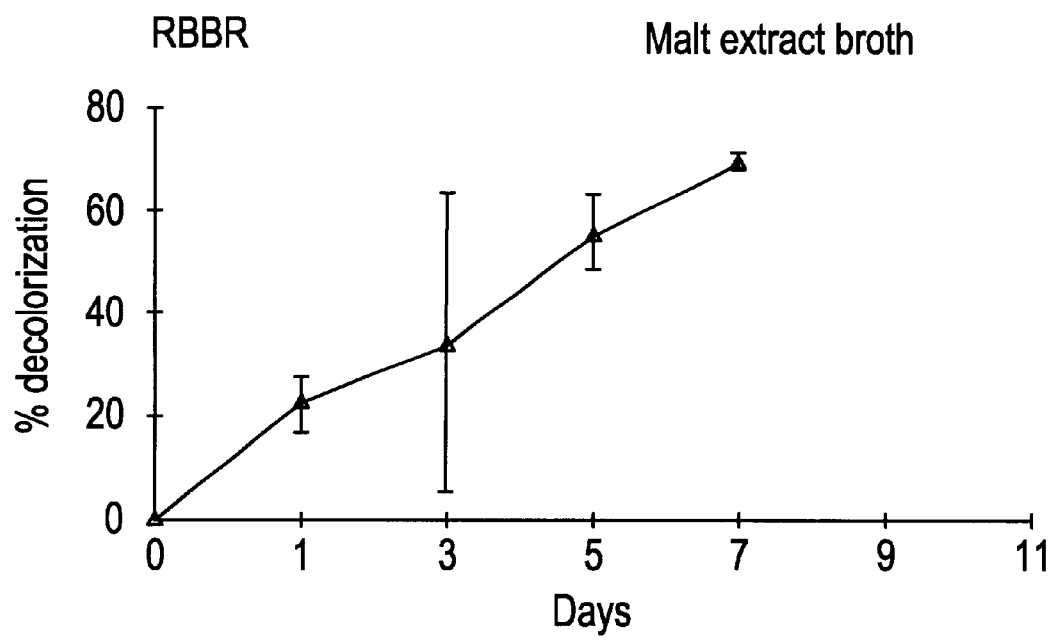
FIG. 1g. depicts decolorization of Remazol Brilliant Blue R by the fungus *Flavodon flavus*, NIOCC isolate #312, grown in the malt extract broth. The results are given as the difference in percent decolorization between heat-killed control and the experimental live cultures.
Figure 2A:
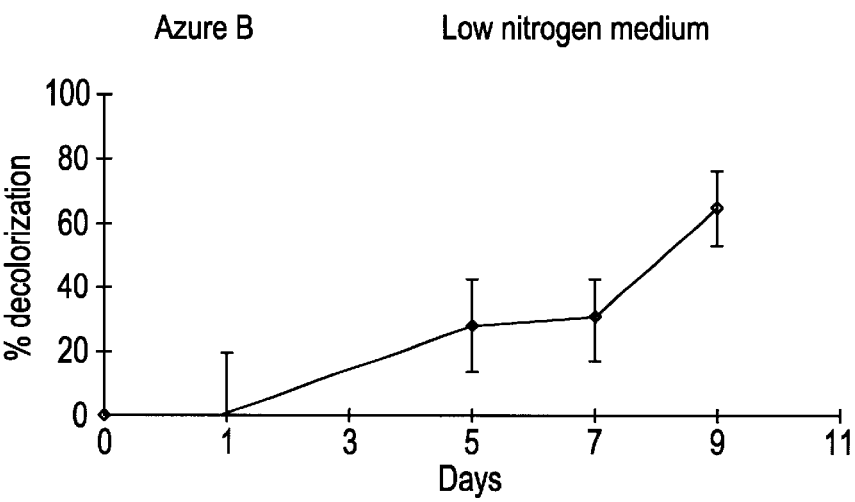
FIG. 2a. depicts decolorization of Azure-B by the fungus *Flavodon flavus*, NIOCC isolate #312, grown in low nitrogen medium. The results are given as the difference in percent decolorization between heat-killed control and the experimental live cultures.
Figure 2B:
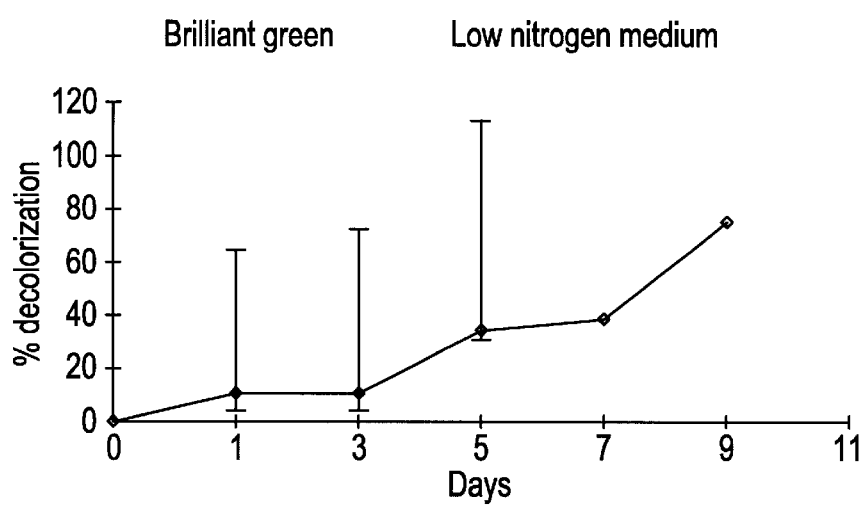
FIG. 2b. depicts decolorization of Brilliant green by the fungus *Flavodon flavus*, NIOCC isolate #312, grown in low nitrogen medium. The results are given as the difference in percent decolorization between heat-killed control and the experimental live cultures.
Figure 2C:
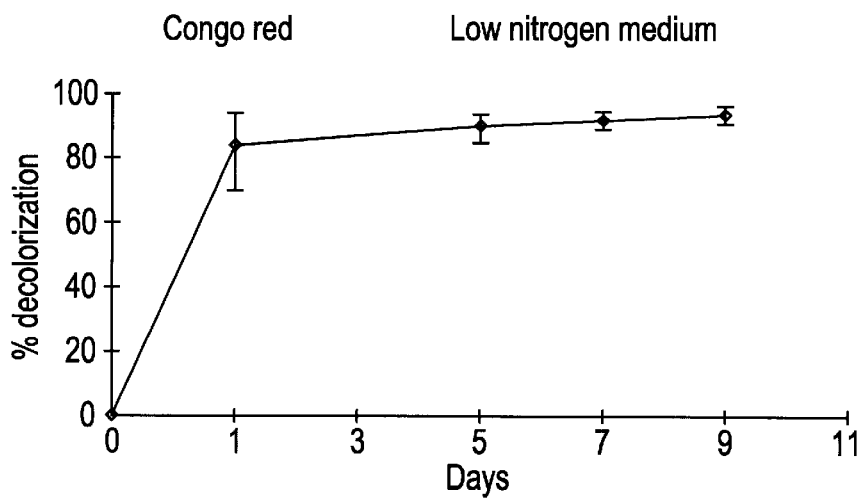
FIG. 2c. depicts decolorization of Congo red by the fungus *Flavodon flavus*, NIOCC isolate #312, grown in low nitrogen medium. The results are given as the difference in percent decolorization between heat-killed control and the experimental live cultures.
Figure 2D:
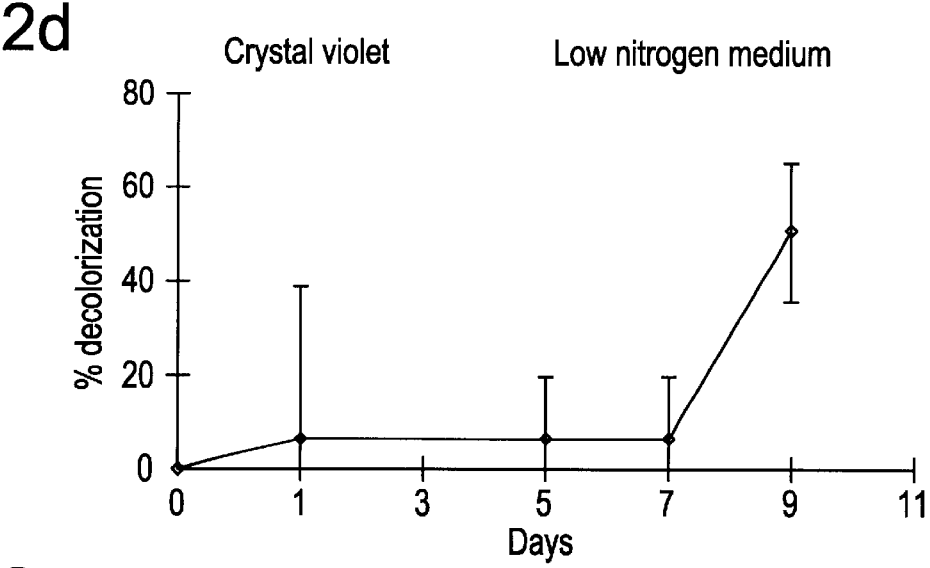
FIG. 2d. depicts decolorization of Crystal violet by the fungus *Flavodon flavus*, NIOCC isolate #312, grown in low nitrogen medium. The results are given as the difference in percent decolorization between heat-killed control and the experimental live cultures.
Figure 2E:
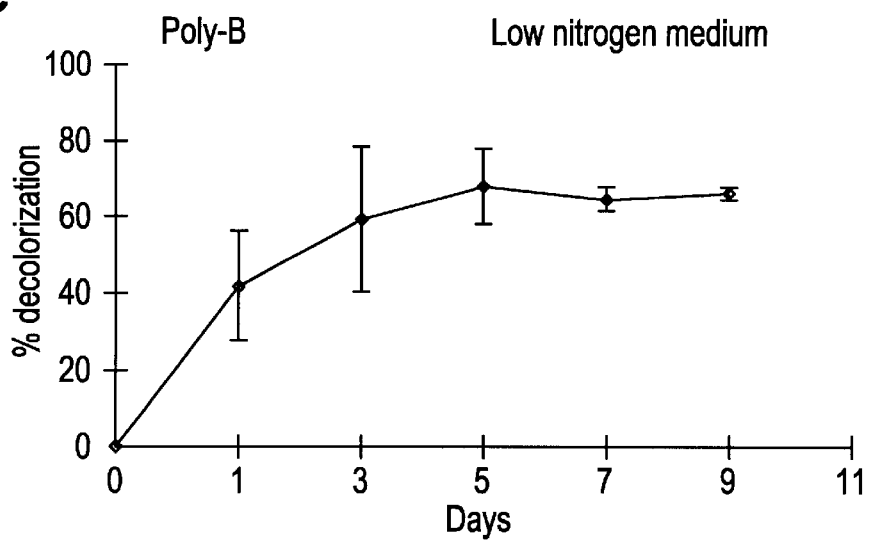
FIG. 2e. depicts decolorization of Poly-R by the fungus *Flavodon flavus*, NIOCC isolate #312, grown in low nitrogen medium. The results are given as the difference in percent decolorization between heat-killed control and the experimental live cultures.
Figure 2F:
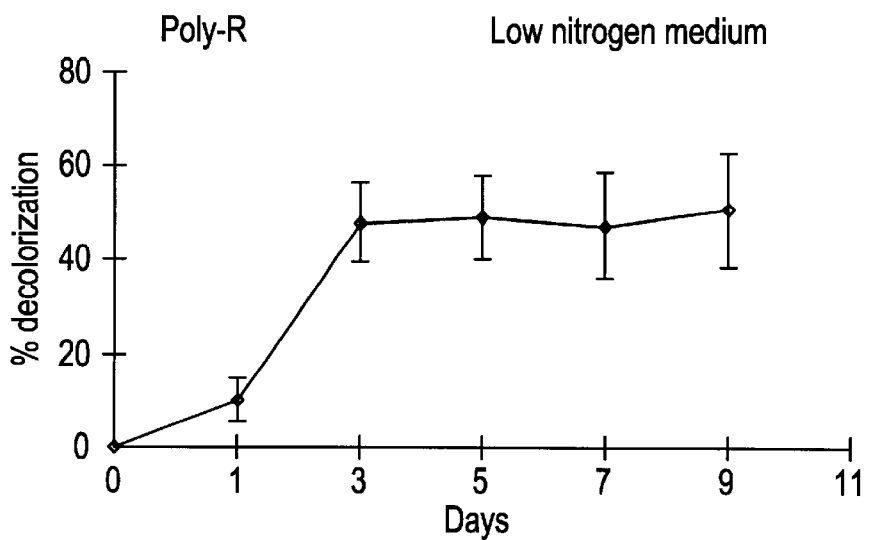
FIG. 2f. depicts decolorization of Poly-B by the fungus *Flavodon flavus*, NIOCC isolate #312, grown in low nitrogen medium. The results are given as the difference in percent decolorization between heat-killed control and the experimental live cultures.
Figure 2G:
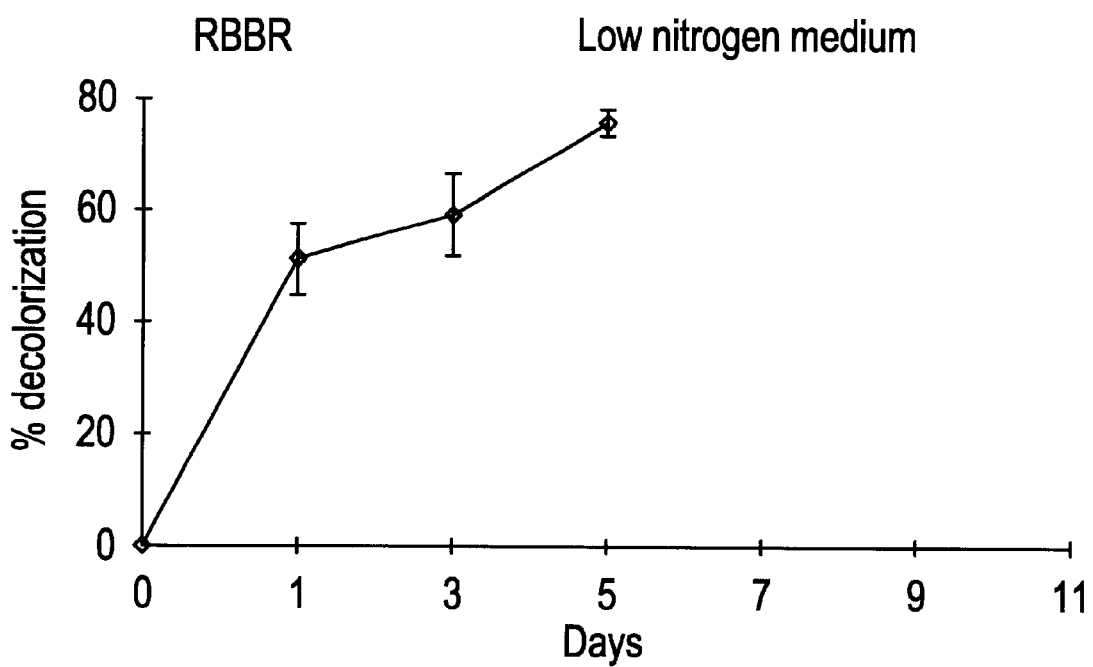
FIG. 2g. depicts decolorization of Remazol Brilliant Blue R by the fungus *Flavodon flavus*, NIOCC isolate #312, grown in low nitrogen medium. The results are given as the difference in percent decolorization between heat-killed control and the experimental live cultures.
Figure 3A:
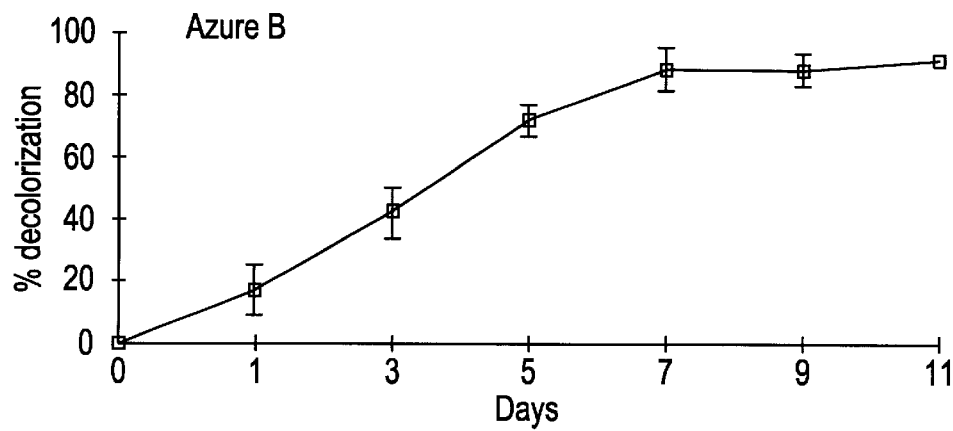
FIG. 3a. depicts decolorization of Azure-B by the fungus *Flavodon flavus*, NIOCC isolate #312, grown in low nitrogen medium prepared with half-strength artificial sea water. The results are given as the difference in percent decolorization between heat-killed control and the experimental live cultures.
Figure 3B:
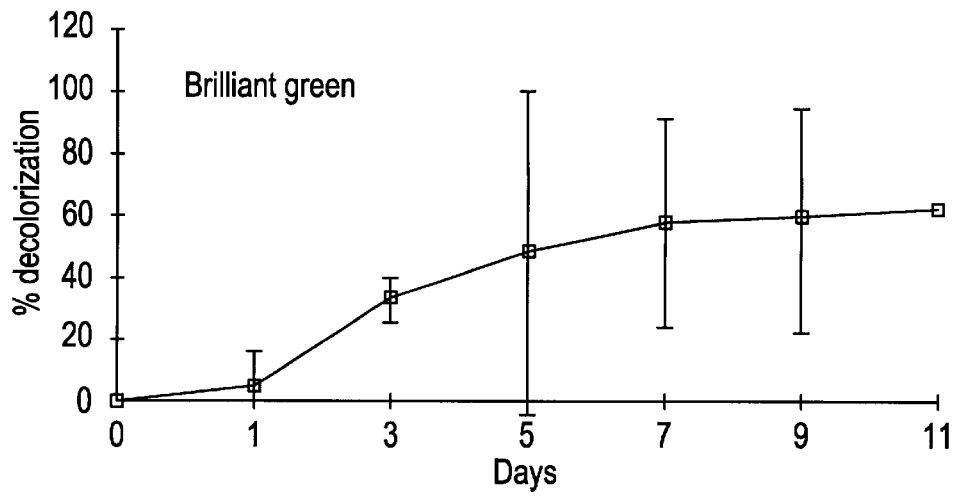
FIG. 3b. depicts decolorization of Brilliant green by the fungus *Flavodon flavus*, NIOCC isolate #312, grown in low nitrogen medium prepared with half-strength artificial sea water. The results are given as the difference in percent decolorization between heat-killed control and the experimental live cultures.
Figure 3C:
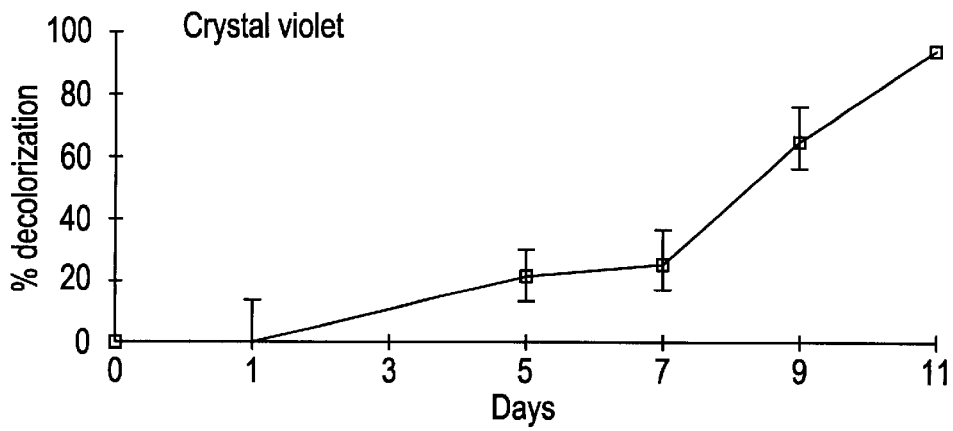
FIG. 3c. depicts dcolorization of Congo red by the fungus *Flavodon flavus*, NIOCC isolate #312, grown in low nitrogen medium prepared with half-strength artificial sea water. The results are given as the difference in percent decolorization between heat-killed control and the experimental live cultures.
Figure 3D:
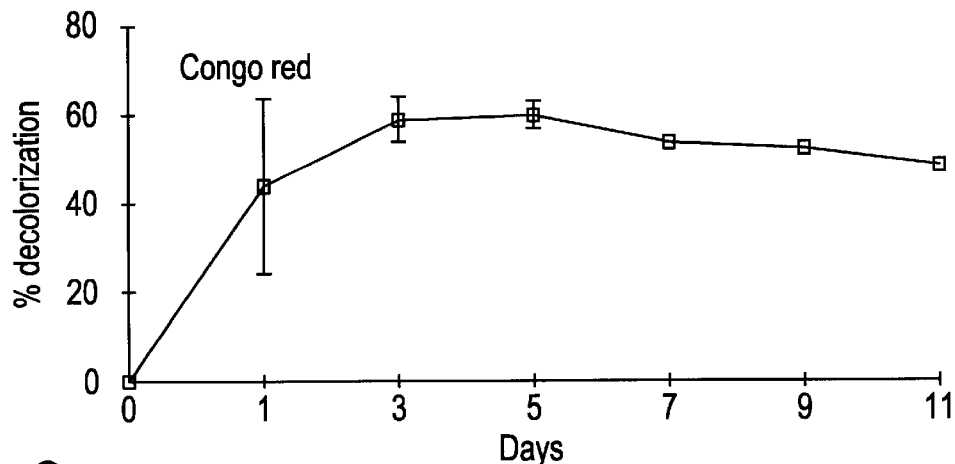
FIG. 3d. depicts decolorization of Crystal violet by the fungus *Flavodon flavus*, NIOCC isolate #312, grown in low nitrogen medium prepared with half-strength artificial seawater. The results are given as the difference in percent decolorization between heat-killed control and the experimental live cultures.
Figure 3E:
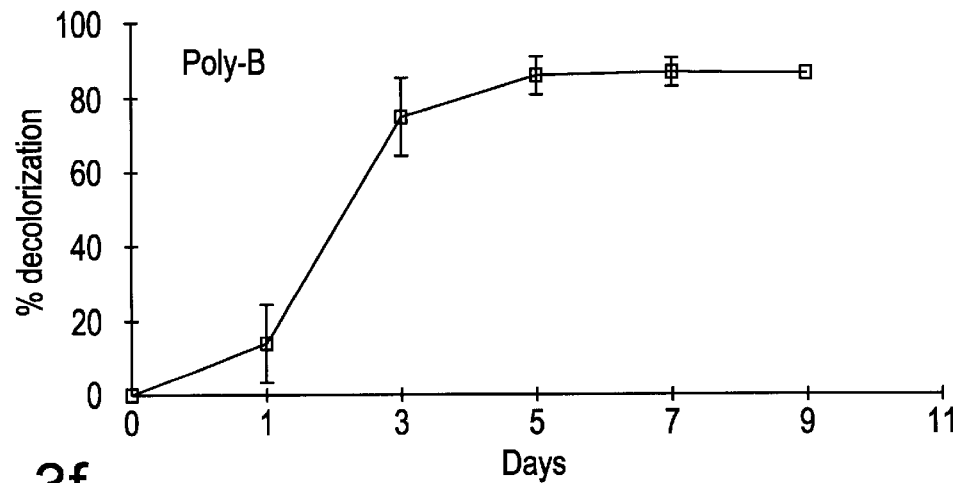
FIG. 3e. depicts decolorization of Poly-R by the fungus *Flavodon flavus*, NIOCC isolate #312, grown in low nitrogen medium prepared with half-strength artificial sea water. The results are given as the difference in percent decolorization between heat-killed control and the experimental live cultures.
Figure 3F:
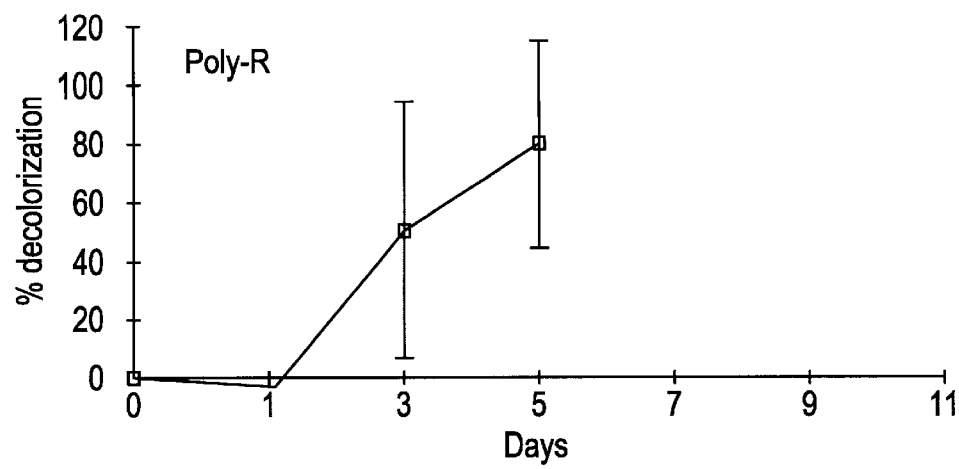
FIG. 3f. depicts decolorization of Poly-B by the fungus *Flavodon flavus*, NIOCC isolate #312, grown in low nitrogen medium. The results are given as the difference in percent decolorization between heat-killed control and the experimental live cultures.
Figure 3G:
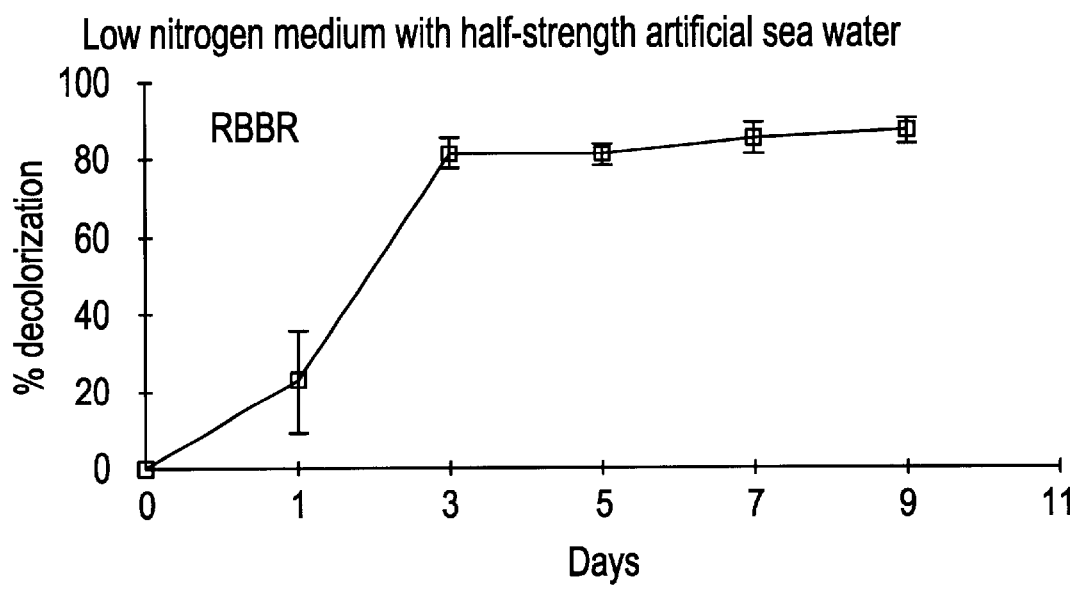
FIG. 3g. depicts decolorization of Remazol Brilliant Blue R by the fungus *Flavodon flavus*, NIOCC, isolate #312, grown in low nitrogen medium prepared with half-strength artificial sea water. The results are given as the difference in percent decolorization between heat-killed control and the experimental live cultures.
Figure 4A:
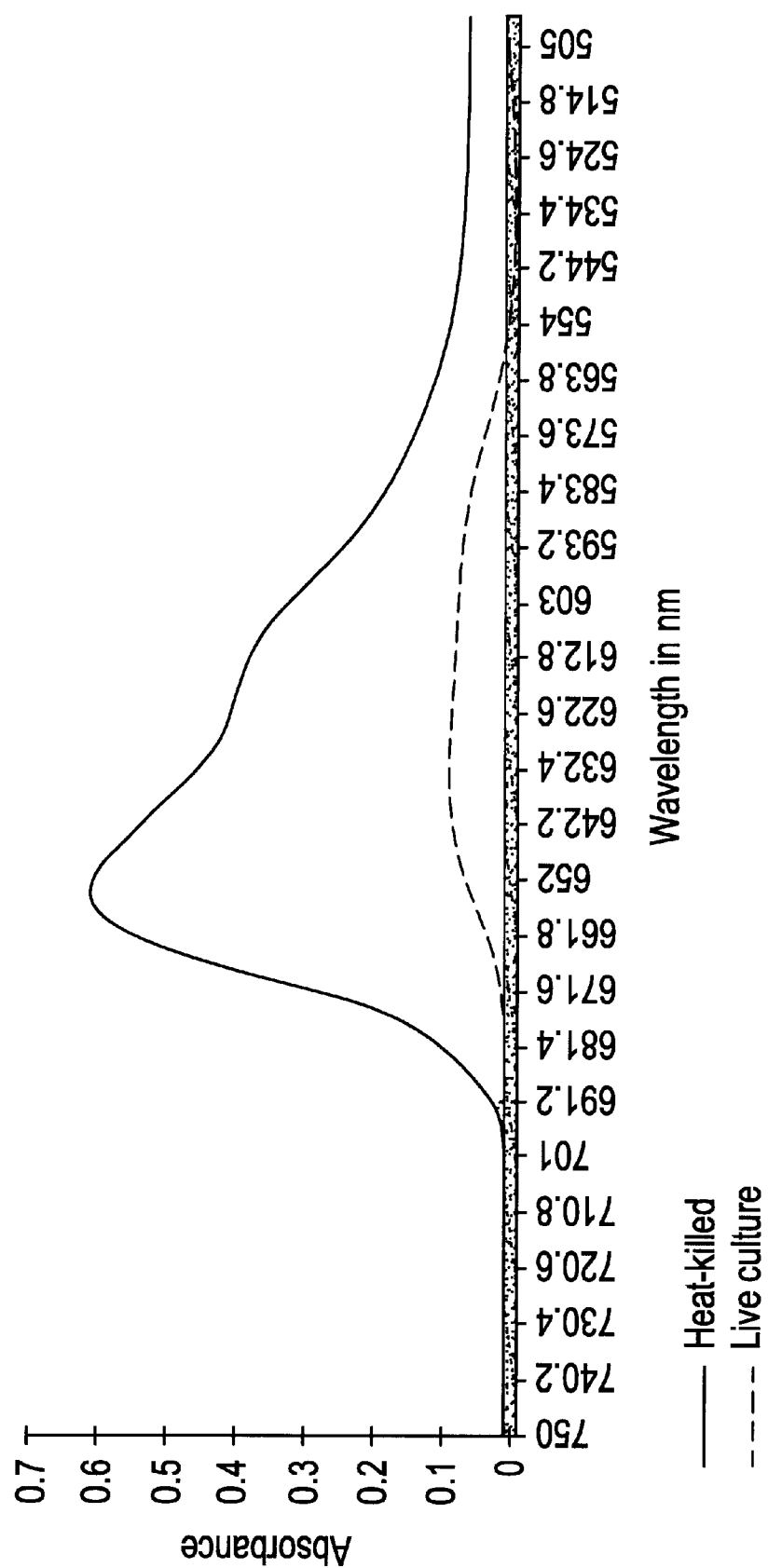
FIG. 4a. depicts spectrum of undegraded Azure-B in control heat-killed culture and the same after degradation in live culture of the isolate #312.
Figure 4C:
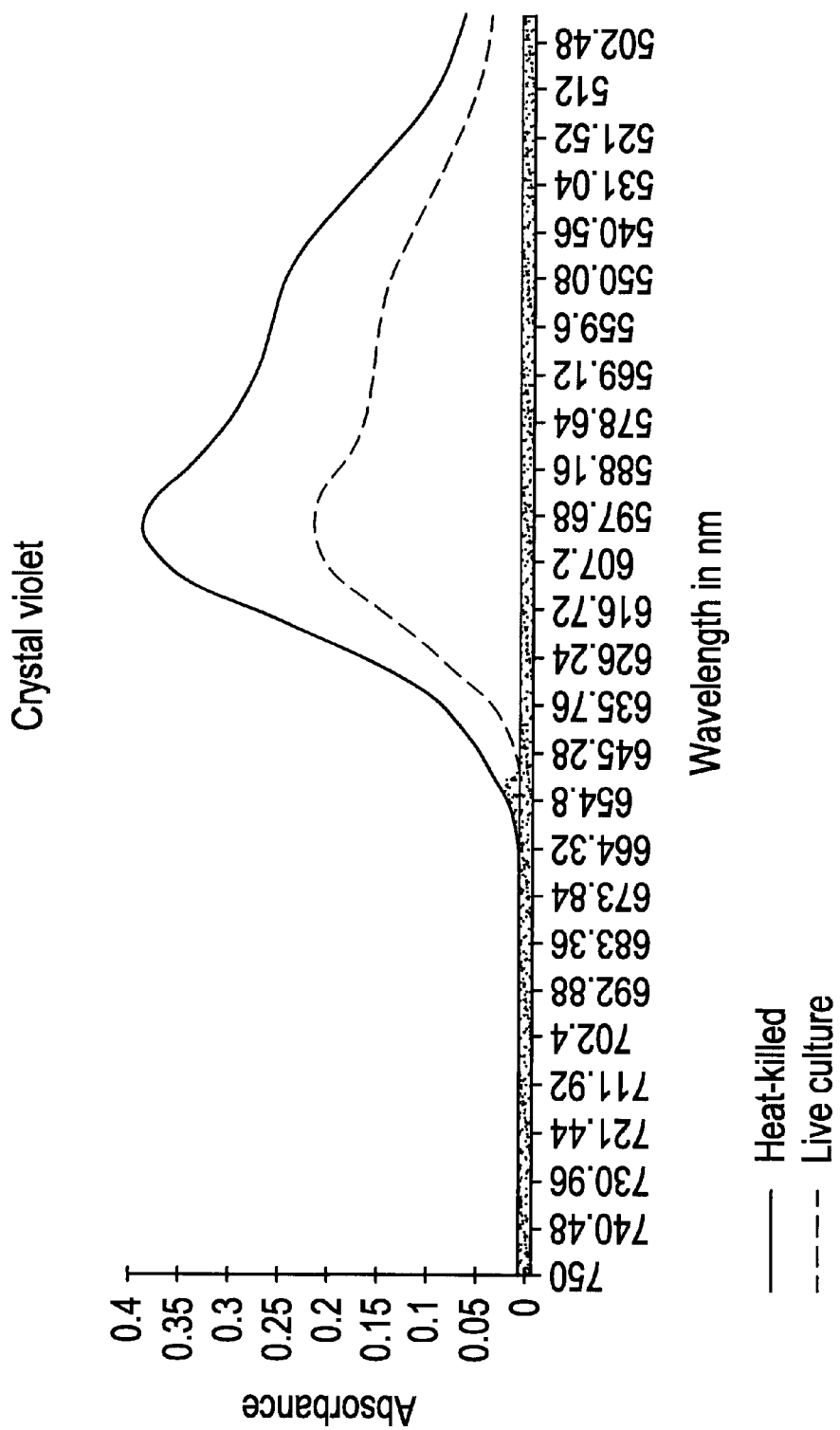
FIG. 4c. depicts spectrum of undegraded Crystal violet in control heat-killed culture and the same after degradation in live culture of the isolate #312.
Figure 4D:
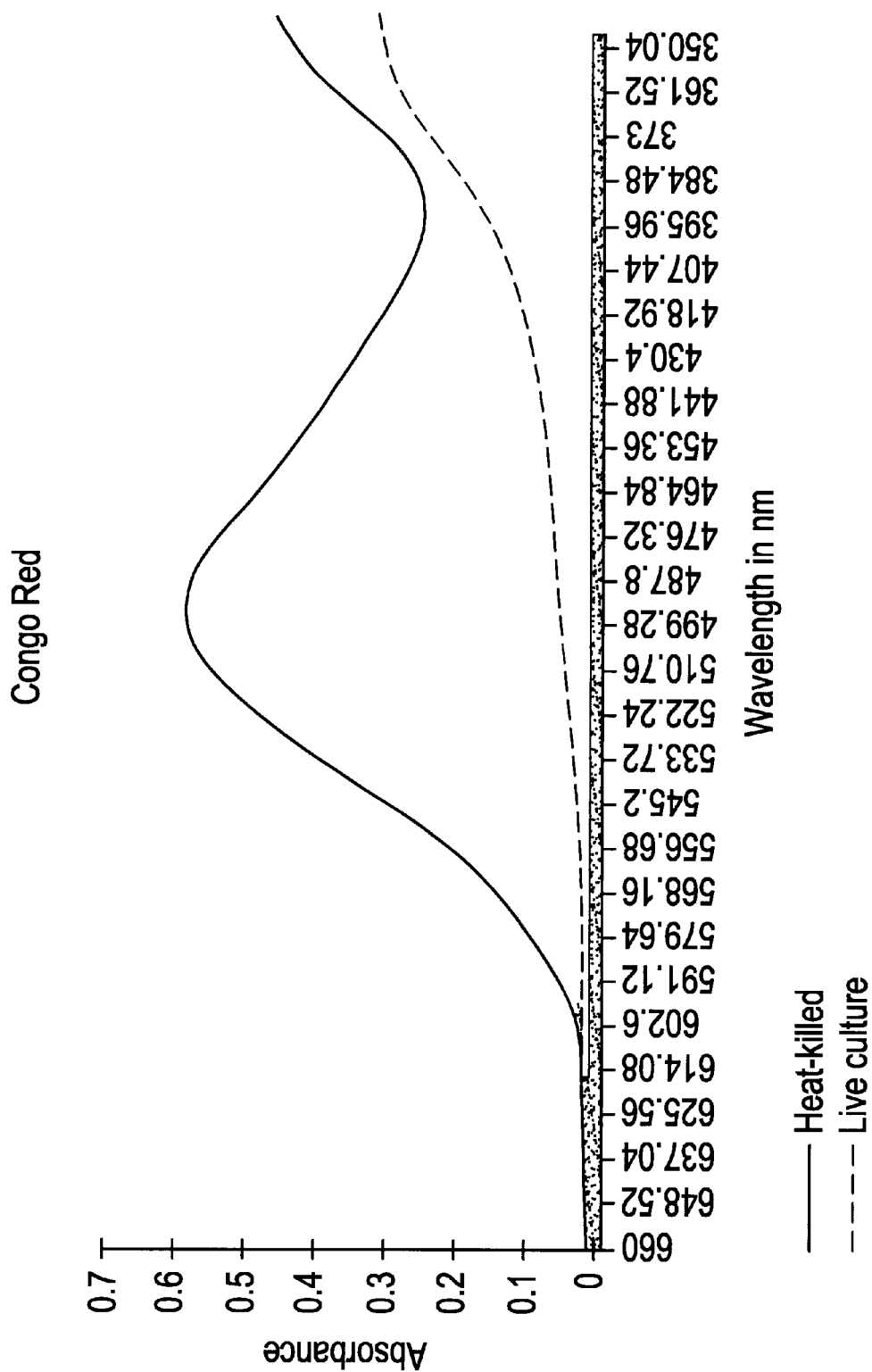
FIG. 4d. depicts spectrum of undegraded Congo red in control heat-killed culture and the same after degradation in live culture of the isolate #312.
Figure 4E:
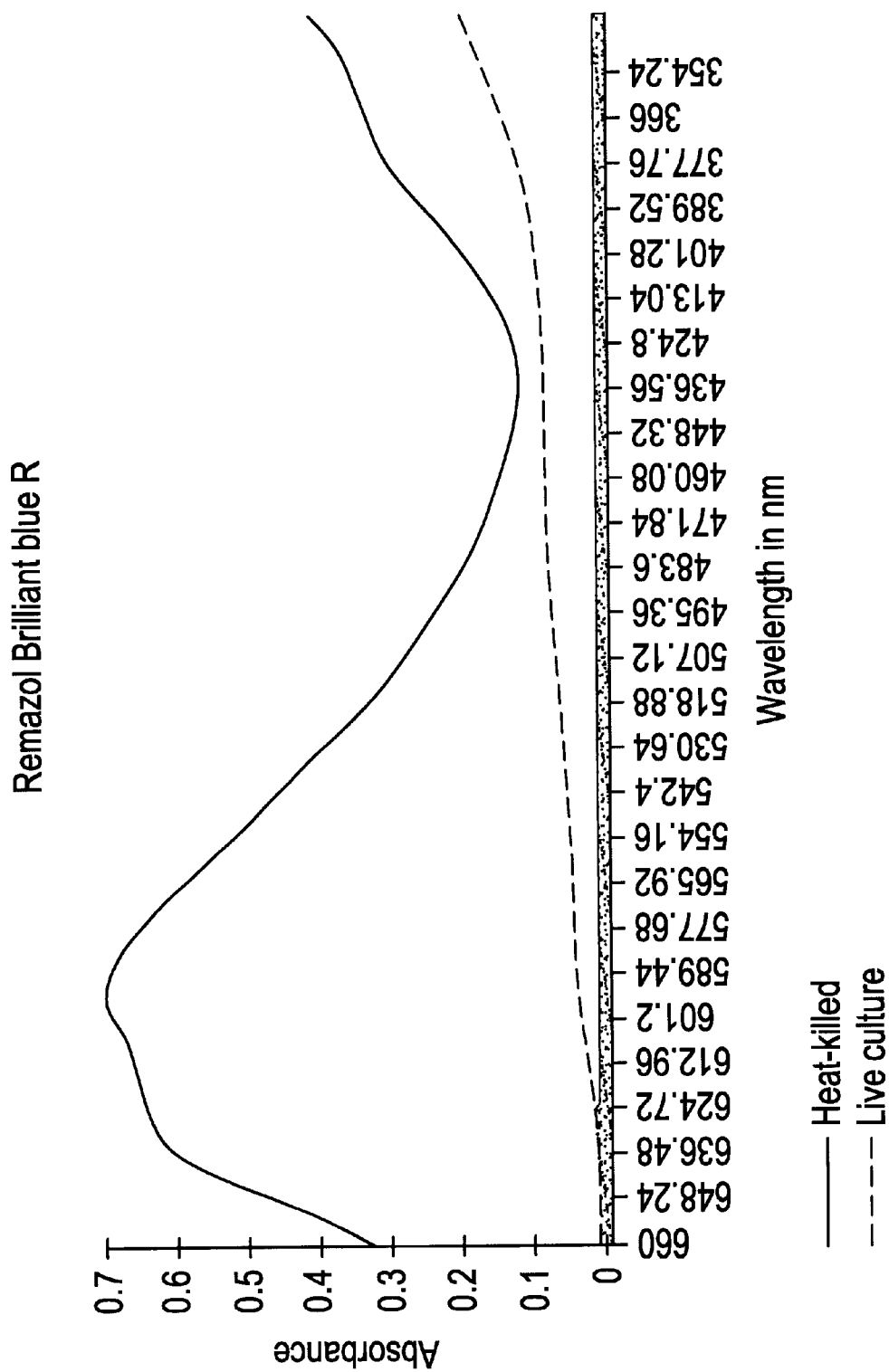
FIG. 4e. depicts spectrum of undegraded Remazol Brilliant Blue R in control heat-killed culture. and the same after degradation in live culture of the isolate #312.

The fungus of the present invention *Flavodon flavus* has been deposited in the National Institute of Oceanography, Dona Paul, Goa 400004, India, and allotted the accession No. NIOCC 312. The same fungus is deposited at Agricultural Research Service Culture Collection (NRRL), 1815 North University Street, Peoria, Ill. 61604, U.S.A., bearing accession No NRRL 30302.

The following examples represent certain specific embodiments of the invention. The scope of the invention is not limited to the examples given hereinbelow. Various modifications that would be apparent to those in the art are deemed to be included within the scope of the invention.

EXAMPLES

Example-1

A non-sporulating form of the fungus was isolated from decaying brown leaves of sea grass from the intertidal of a lagoon in Kavaratti island of the Lakshadweep archipelago (10°30'–11.0°N Lat, 72.0°–73.0°E, Long.) off the west coast of India in the Arabian sea. Discs (0.5 cm diameter) from brown decaying leaves of the sea grass *Thalassia hemprichii* (Ehrenberg) Ascerson were surface sterilized in 0.5% sodium hypochlorite for 3 min, washed in sterile sea water three times for a duration of two minutes each. The discs were placed on synthetic medium prepared with 50% sea water and supplemented with 2 g agar powder, 0.02% polymeric dye Poly-R478, 10,000 units of sodium benzyl penicillin and 0.5 g streptomycin sulfate per 100 ml medium. White and fluffy fungal colonies, which decolorized Poly-R, were isolated. The fungus was given an accession number NIOCC isolate 312. This fungus did not sporulate in this synthetic medium. However, it produced fertile basidiomata on medium containing alpha cellulose or after a long incubation in malt extract agar medium. Based on fertile basidiomata using the key of Ryvarden and Johansen, it was identified as *Flavodon flavus* (KI) Ryv.

Since the strain #312 was isolated from a marine habitat, the effect of salinity on its growth can be studied by growing in medium prepared with 100% sea water, 50% sea water and in distilled water. Growth in natural medium such as malt extract broth and synthetic media were compared for this purpose. Malt extract broth contains 2% malt extract and 0.3% peptone in distilled water or seawater of various salinities. Instead of natural seawater which may not be available to every one, synthetic sea salts of reputed companies can be used in preparing artificial sea water. The applicants used Instant Ocean salts obtained from Aquarium Systems, Mentor, Ohio, USA. By dissolving 15 g and 30 g of Instant Ocean salts in 1 liter of distilled water, salinity equivalents of 1.5 and 3.0% were obtained. The former is referred to as 50% artificial sea water or half-strength sea water. The synthetic media can be prepared in distilled water or 50% artificial sea water containing 1% glucose as carbon source, 2.4 mM ammonium tartrate as the nitrogen source, thiamin, trace metal solution, macro element solution containing sodium, potassium and manganese salts, Tween 80, veratryl alcohol and 20 mM sodium acetate buffer at pH 4.5. This synthetic medium is referred to as low nitrogen medium. Growth of the fungus is measured as mycelial dry weight produced at the end of 10 days incubation in various media. For determination of dry weight, the contents of three flasks are vacuum filtered through tared Whatman GF/C filter papers, rinsed with 100 ml of distilled water to remove salts and dried to a constant weight and the net mycelial dry weight is calculated.

TABLE 1

* The weight of fungus per 10 ml of medium in 10 days.

| Medium | With distilled water | With 50% artificial sea water |
|---|---|---|
| Malt extract broth | 10.3 mg | 12.9 mg |
| Low Nitrogen medium | 23 mg | 44 mg |

The example given here shows that the fungus *F. flavus* grows much better in the presence of 50% artificial sea water and thus can be used in presence of synthetic salts or in estuarine conditions.

Example-2

The ability of *F. flavus*, NIOCC isolate 312, to degrade and decolorize synthetic dyes was tested in nutrient rich medium such as malt extract broth. Preparation of medium was done as described in Example 1. Sterile media are dispensed in 9 ml amounts into 125 ml sterile rubber-stoppered Erlenmeyer flasks. The flasks are inoculated with 1 ml of fungal inoculum. For inoculum preparation, mycelial mats grown in malt extract broth (25 ml in 250 ml foam-plugged Erlenmeyer flasks) for 10 days at room temperature were washed twice with 150 ml of sterile water and blended in 20 ml of low nitrogen medium using a Sorvall blender (with four 30-seconds spurts). One ml of this blended mycelium (equivalent to 3 mg initial dry weight of mycelium) was used for inoculating media in 125 ml Erlenmeyer flasks. The flasks are flushed with 100% $O_2$ at the time of inoculation and every alternate day thereafter. Culture flasks are incubated at room temperature. Individual dye solutions were added to 4-day-old cultures of *F. flavus*, to give final dye concentrations of 0.02%. The dyes used were Azure B, Brilliant Green, Crystal Violet, Congo Red, Remazol Brilliant Blue R, Poly B-411 and Poly R-478. Stock solutions of dyes were prepared in distilled water and filter sterilized. Autoclaved cultures supplemented with dyes served as heat-killed controls. Aliquots (0.5 ml) of culture supernatants from experimental cultures and from heat-killed controls were removed aseptically at 2-day intervals, diluted appropriately with distilled water and the changes in absorbance maxima for the different dyes were measured using a Varian Cary 1 Bio UV/Visible spectrophotometer (Varian, Australia). Azure B was measured at 647 nm, Brilliant Green at 625 nm, Congo Red at 495 nm, Crystal Violet at 590 nm, and Remazol Brilliant Blue R at 595 nm. (Heinfling, A., M. Bergbauer, and U. Szewzyk. 1997. Biodegradation of azo and phthalocyanine dyes by *Trametes versicolor* and *Bjerkandera adusta*. Applied Microbiology and Biotechnology. 48:261–266). Decolorization of Poly B and Poly R was monitored by determining the absorption ratio at 593/483 nm and 513/362 nm respectively (Gold, M. H., J. K. Glenn, and M. Alic. 1988. Use of polymeric dyes in lignin biodegradation assays. Methods in Enzymology. 161: 74–78). The results are calculated as the difference in percent decolorization between heat-killed and experimental cultures. Degradation of various dyes was also monitored by comparing the changes in the visible spectra of native dyes in heat-killed culture fluids with that of decolorized dyes in experimental culture fluids at 400–800 nm. This was carried out at the end of the experiment.

Accordingly, FIGS. 1*a*–1*g* shows the percentage of decolorization of various dyes by *F. flavus*, NIOCC isolate 312 when grown in simple natural medium such as malt extract broth. Azure B and Remazol Brilliant Blue R were decolorized up to 60% within 7 days. Decolorization of Poly B is delayed initially but the final percentage of decolorization is 60%.

Example-3

Decolorization of various dyes by *F. flavus*, NIOCC isolate 312, was tested in synthetic medium such as low nitrogen medium prepared with distilled water. Preparation of synthetic medium was done as described in Example-1. Inoculation, oxygenation and incubation were done as described in Example-2. Experimental procedures of addition of dyes and monitoring the decolorization were same as described in Example-2.

Accordingly, FIGS. 2*a*–2*g* show that about 70% decolorization of all the dyes took place within 7 days in low nitrogen medium prepared with distilled water.

Example-4

Decolorization of various dyes by *F. flavus*, NIOCC isolate 312, was tested in synthetic medium such as low nitrogen medium prepared with half-strength artificial sea water. Artificial sea water was prepared by dissolving 15 g of Instant Ocean salts, as per the manufacturer's instructions (Instant Ocean of Aquarium Systems, Mentor, Ohio) in 1 litre of distilled water to get salinity equivalent of 15 parts per thousand and filtered through a GF/C filter paper. The normal salinity of sea water is 30 parts per thousand.

Preparation of low nitrogen medium was done as described in Example-1. Inoculation, oxygenation and incubation were done as described in Example-2. Experimental procedures for addition of dyes and monitoring the decolorization were same as described in Example-2.

Accordingly, FIGS. 3*a*–3*g* show decolorization of various dyes by *F. flavus*, NIOCC isolate 312, when grown in low nitrogen medium prepared with 50% artificial sea water. More than 80% decolorization of all dyes was achieved within 7 days in this medium.

The fungus *F. flavus* also degraded the various dyes as seen by changes in the visible spectra of native dyes in experimental cultures in comparison with heat-killed control culture fluids. FIGS. 4*a*–4*e* shows complete degradation of some of the dyes by the fungus *F. flavus* when grown in low nitrogen medium with 50% artificial sea water.

Example-5

In order to show that degradation of dyes is brought about by production of lignin-modifying enzymes in malt extract broth, the fungus was grown in this medium as described in Example-2. Inoculation, oxygenation and incubation were carried out as described in Example-2.

Contents of three flasks were filtered on different days of incubation using Whatman GF/C filters and the extracellular fluids were analysed for lignin-modifying enzymes such as manganese-dependent peroxidase (MNP), lignin peroxidase (LIP) and laccase. A convenient assay for MNP involves monitoring the enzyme's oxidation of Mn(II) to Mn(III). The reaction mixture contains enzyme, 0.1 M sodium tartrate buffer (pH 5.0), 0.1 M $H_2O_2$ and 0.1 mM $MnSO_4$. Reactions are initiated by the addition of $H_2O_2$ and increase in absorbance at 238 am is monitored during the first 5–30 sec of reaction. One unit of MNP oxidizes 1 μmol of Mn(II)/min (Paszczyniski, A, R. L. Crawford, and V.-B. Huynh. 1988. Manganese peroxidase of *Phanerochaete chrysosporium*: purification. Methods in Enzymology. 161: 264–270). Lignin peroxidase catalyzes oxidation of veratryl alcohol to veratraldehyde by $H_2O_2$. The reaction mixture for assay contains veratryl alcohol, tartaric acid at pH 3.0, 8 mM $H_2O_2$ and enzyme solution. Increase in absorbance at 310 nm is monitored for 1 min. One unit of enzyme is defined as 1 μmol of veratryl alcohol oxidized per min (Tien, M., and T. K. Kirk. 1988. Lignin peroxidase of *Phanerochaete chrysosporium*. Methods in Enzymology. 161: 239–249). Lacasse activity was determined by using the substrate 2,2'azino-bis(3-ethylbenzthiazoline-6-sulfonic acid), in 0.1 M glycine buffer at pH 3.0. The reaction was monitored by measuring change in absorbance at 405 nm for 5 min. The enzyme units are expressed as nkatals/L (Niku-Paavola, M-L., E. Karhunen, P. Salola and V. Raunio. 1988. Lignilolytic enzymes of the white-rot fungus *Phlebia radiata*. Biochemical Journal. 254: 877–884). One katal is defined as one molar extinction coefficient of product formed per second.

Figure 5A:
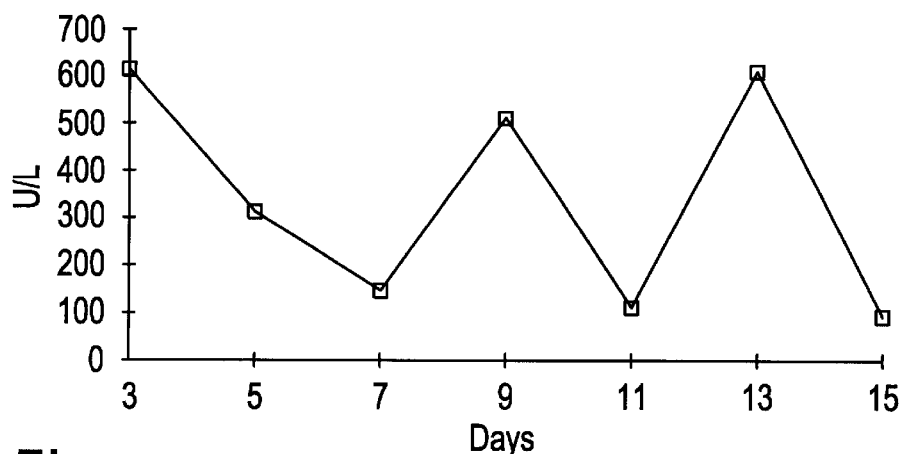
FIG. 5a. depicts production of manganese-dependent peroxidase by the isolate #312 when grown in the malt extract broth medium.

Accordingly, FIG. 5a represents production of MNP in malt extract broth prepared with distilled water by the fungus *F. flavus*, NIOCC isolate 312.

Figure 5B:
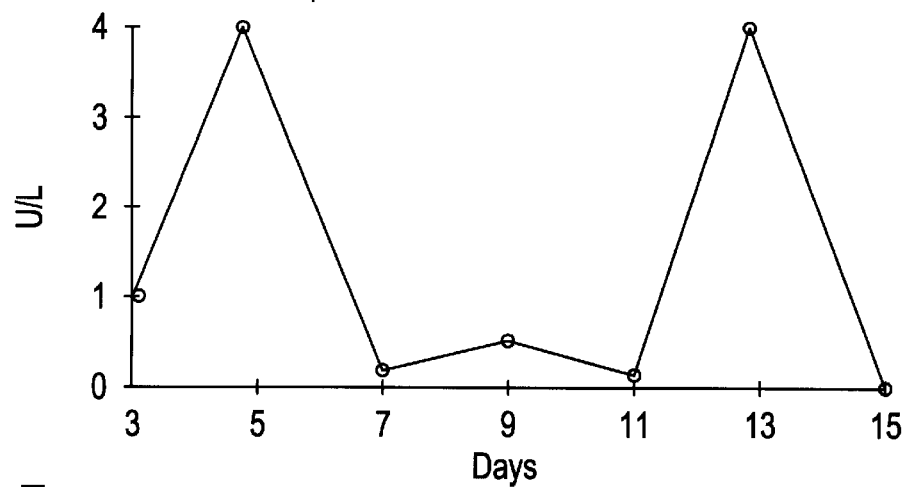
FIG. 5b. depicts production of lignin peroxidase by the isolate #312 when grown in the malt extract broth medium.

Accordingly FIG. 5b represents production of LIP in malt extract broth prepared with distilled water by the fungus *F. flavus*, NIOCC isolate 312.

Figure 5C:
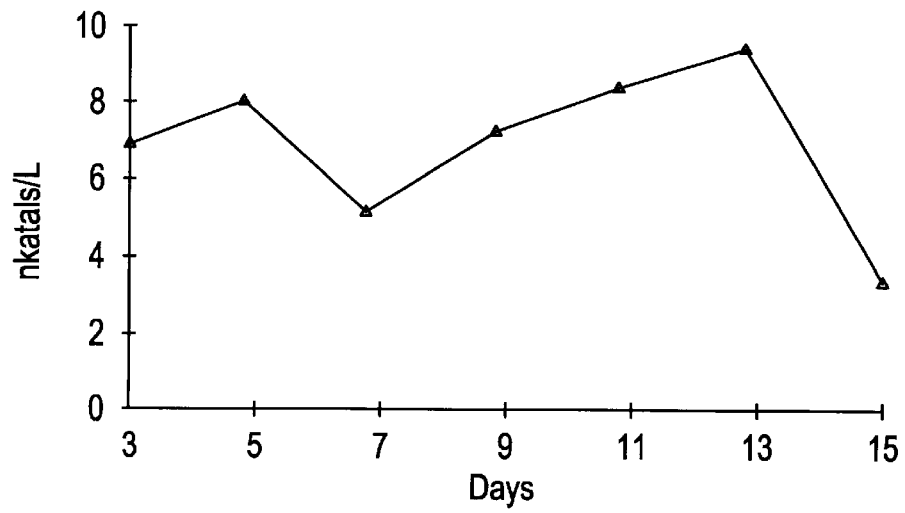
FIG. 5c. depicts poduction of laccase by the isolate #312 when grown in the malt extract broth medium.

Accordingly, FIG. 5c represents production of laccase in malt extract broth prepared with distilled water by the fungus *F. flavus*, NIOCC isolate 312.

Example-6

In order to show that degradation of dyes is brought about by production of lignin-modifying enzymes in synthetic medium such as low nitrogen medium, the fungus was grown in the low nitrogen medium prepared with distilled water as described in Example-1. Inoculation, incubation, oxygenation and sampling of culture filtrates were done as described in Example-5. Enzyme assays of the culture fluids were carried out as described in Example-5.

Figure 6A:
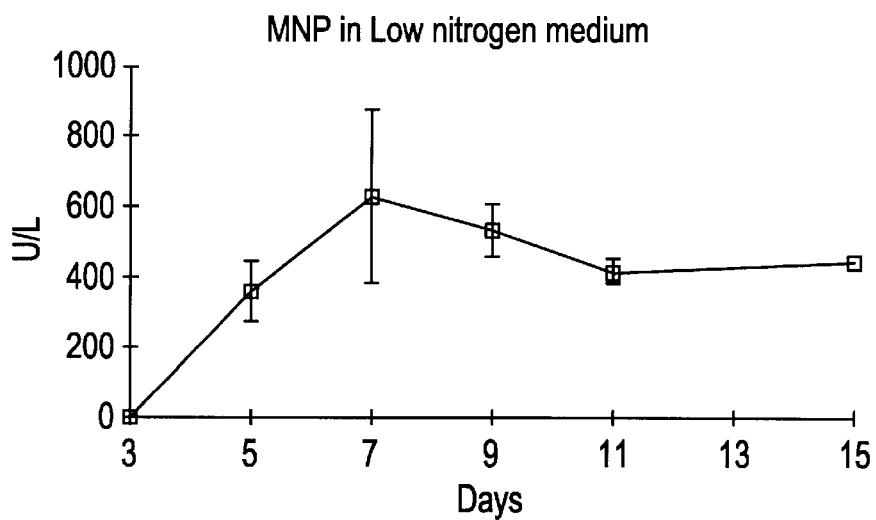
FIG. 6a. depicts production of manganese-dependent peroxidase by the isolate #312 when grown in the low nitrogen medium.

Accordingly FIG. 6a represents production of MNP in low nitrogen medium prepared with distilled water by the fungus *F. flavus*, NIOCC isolate 312.

Figure 6B:
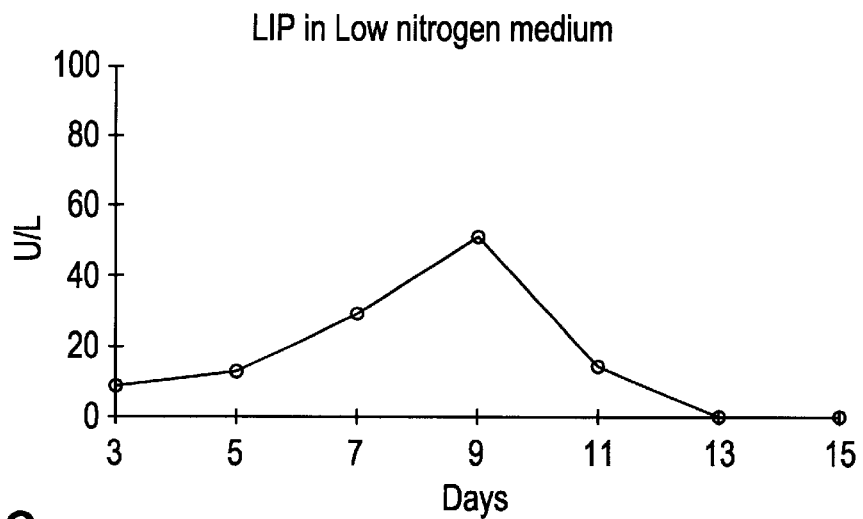
FIG. 6b. depicts production of lignin peroxidase by the isolate #312 when grown in the low nitrogen medium.

Accordingly, FIG. 6b represents production of LIP in this medium by the fungus *F. flavus*, NIOCC isolate 312.

Figure 6C:
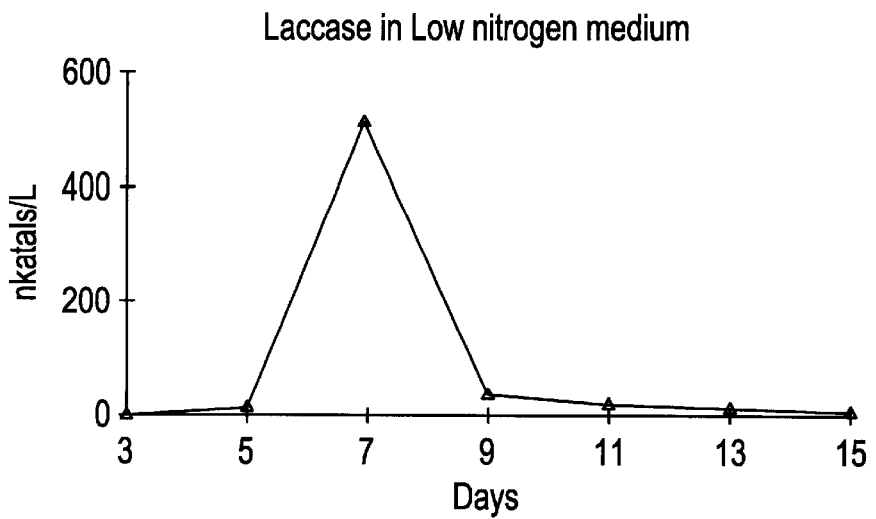
FIG. 6c. depicts production of laccase by the isolate #312 when grown in the low nitrogen medium.

Accordingly, FIG. 6c represents production of laccase in this medium prepared with distilled water by the fungus *F. flavus*, NIOCC isolate 312.

Example-7

In order to show that degradation of dyes is brought about by production of lignin-modifying enzymes in the presence of salts, the fungus was grown in the low nitrogen medium prepared with half-strength artificial sea water as described in Example-1. Inoculation, incubation, oxygenation and sampling of culture filtrates were done as described in Example-5. Enzyme assays of the culture fluids were carried out as described in Example-5.

Figure 7A:
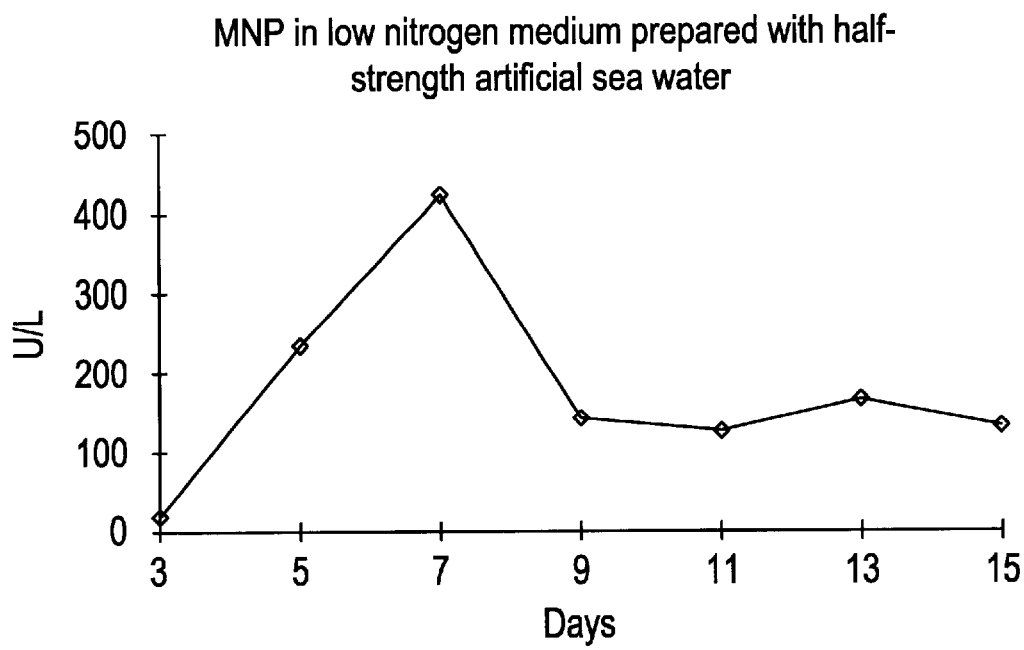
FIG. 7a. depicts production of manganese-dependent peroxidase by the isolate #312 when grown in the low nitrogen medium prepared with half-strength artificial sea water.

Accordingly, FIG. 7a represents production of MNP in low nitrogen medium prepared with 50% artificial sea water by the fungus *F. flavus*, NIOCC isolate 312. No LIP production was detected in this medium.

Figure 7B:
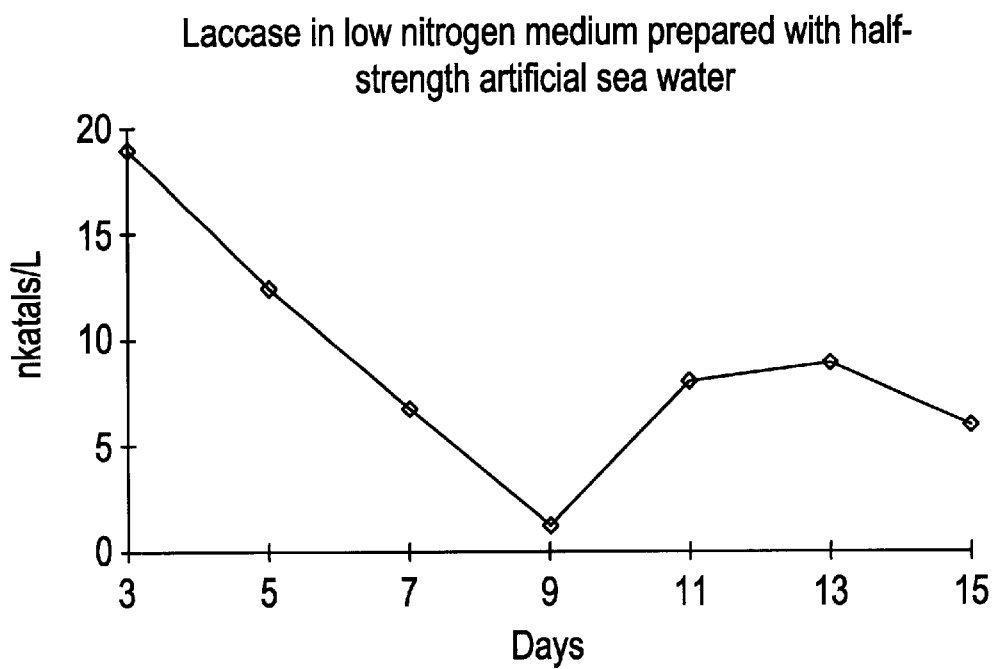
FIG. 7b. depicts production of laccase by the isolate #312 when grown in the low nitrogen medium prepared with half-strength artificial sea water.

Accordingly, FIG. 7b represents production of laccase in low nitrogen medium prepared with 50% artificial sea water by the fungus *F. flavus*, NIOCC isolate 312.

Example-8

Wood and other lignocellulosics are natural substrates for ligninolytic fungi. Therefore, lignin-modifying enzyme production was compared in cultures grown in sugarcane bagasse, which is an inexpensive raw material for large-scale application of this fungus for its potential use in field trials. As the above examples 5, 6, and 7 showed, the degradation of dyes is brought about in various media by production of lignin-modifying enzymes in these media, we wanted to show production of these enzymes in bagasse medium also if it were to be used for application in field trials.

For preparing media with lignocellulosics as the sole carbon/nitrogen/energy source, sugarcane bagasse powder (16 screen mesh/sq. in) was added at 1% final concentration in distilled water. To minimize contamination by residual sugars, the sugarcane bagasse was washed under running tap water for 12 h, followed by a wash with three volumes of distilled water and dried at room temperatures.

The sugarcane bagasse medium was inoculated, oxygenated, incubated and sampled as described in Example-5. The extracellular culture fluids were assayed for MNP, LIP and laccase as described in Example-5.

Figure 8A:
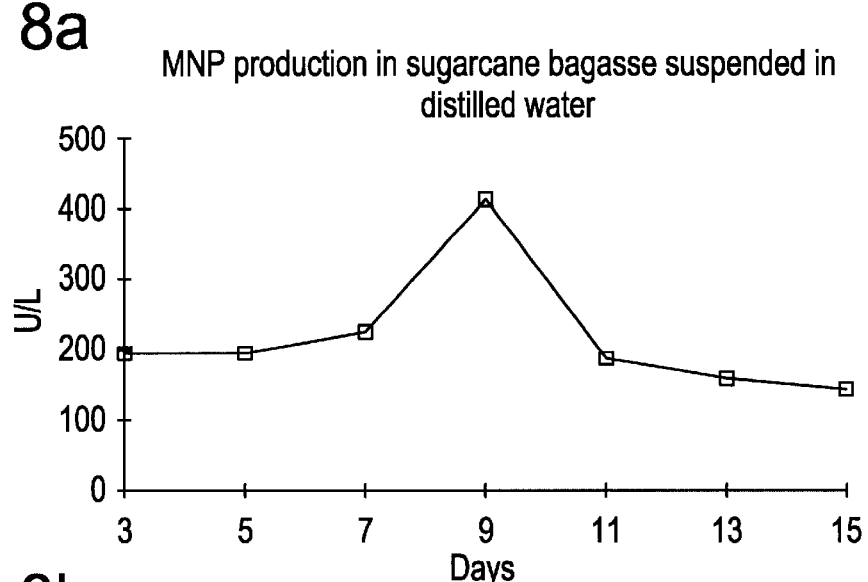
FIG. 8a. depicts production of manganese-dependent peroxidase by the isolate #312 when grown in sugarcane bagasse suspended in distilled water.

Accordingly, FIG. 8a represents production of MNP in sugarcane bagasse medium prepared with distilled water by the fungus *F. flavus*, NIOCC isolate 312.

Figure 8B:
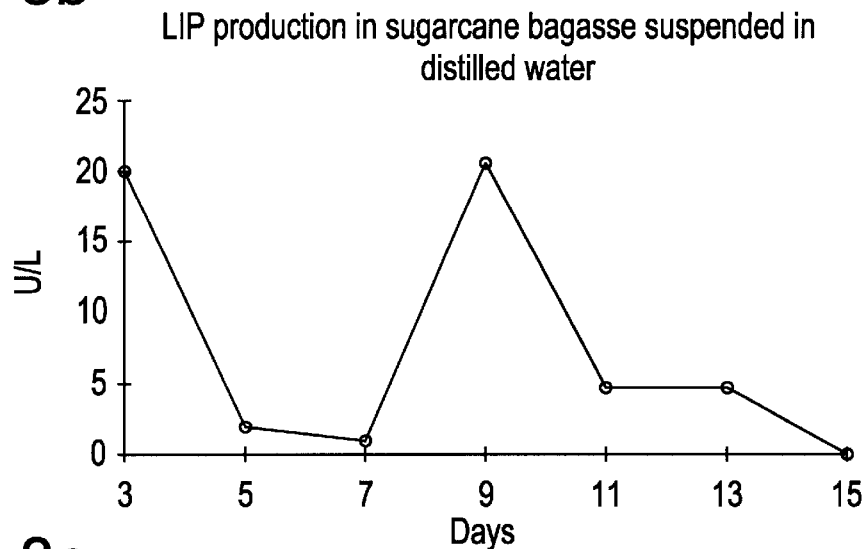
FIG. 8b. depicts production of lignin peroxidase by the isolate #312 when grown in sugarcane bagasse suspended in distilled water.

Accordingly, FIG. 8b represents production of LIP in sugarcane bagasse medium prepared with distilled water by the fungus *F. flavus*, NIOCC isolate 312.

Figure 8C:
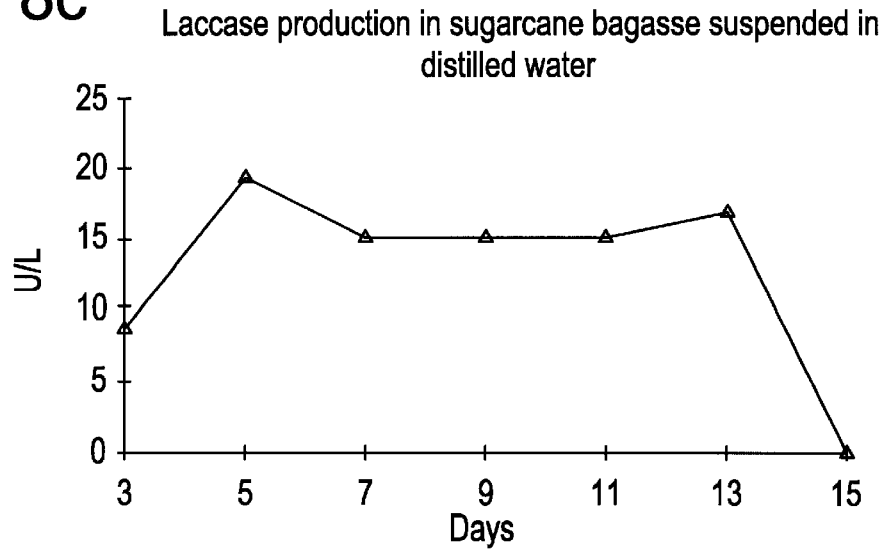
FIG. 8c. depicts production of laccase by the isolate #312 when grown in sugarcane bagasse suspended in distilled water.

Accordingly, FIG. 8c represents production of laccase in sugarcane bagasse medium prepared with distilled water by the fungus *F. flavus*, NIOCC isolate 312.

It is of interest that MNP, which has been shown to be important in delignification of Kraft pulp (Paice, M. G., I. d. Reid, R. Bourbonnais, F. S. Archibald and L. Jurasek. 1993. Manganese peroxidase produced by *Trametes versicolor* during pulp bleaching, demethylates and delignifies kraft pulp. Applied Environmental Microbiology. 59:260–265), and in decolorizing Kraft bleach plant effluents (Michel, F. C. Jr., S. B. Dass, E. A. Grulke, and C. A. Reddy. 1991. Role of manganese peroxidases and lignin peroxidases of *Phanerochaete chrysosporium* in decolorization of kraft bleach plant effluent. Applied Environmental Microbiology. 57: 2368–2375) was produced in highest titres in cultures of *F. flavus* grown with sugarcane bagasse. These results further suggest that sugarcane bagasse can potentially be used for bulk production of biomass of *F. flavus*, NIOCC isolate 312, for possible application in field trials for removal of dyes in dye-containing waste-waters and soil.

Example-9

As the previous example showed production of lignin-modifying enzymes in sugarcane bagasse suspended in distilled water, for its application in presence of salts we can similarly grow the fungus in sugarcane bagasse suspended in half-strength artificial sea water. The medium was inoculated, oxygenated, incubated and sampled as described in the Example-5. The extracellular culture fluids were assayed for MNP, LIP and lacasse as described in Example-5.

Figure 9A:
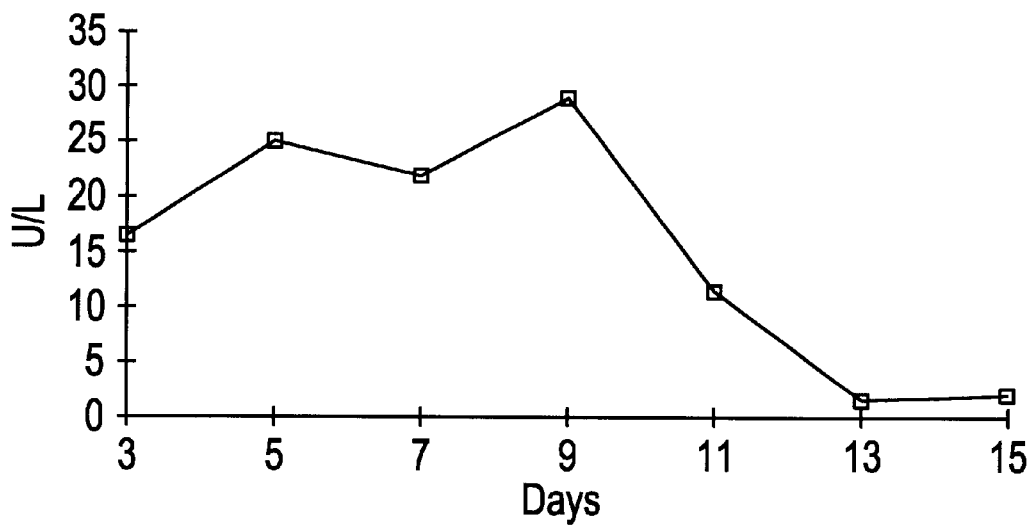
FIG. 9a. depicts production of manganese-dependent peroxidase by the isolate #312 when grown in sugarcane bagasse suspended in half-strength artificial sea water.

Accordingly, FIG. 9a represents production of MNP in sugarcane bagasse medium prepared with half-strength artificial sea water by the fungus *F. flavus*, NIOCC isolate 312. No LIP production was detected in this medium.

Figure 9B:
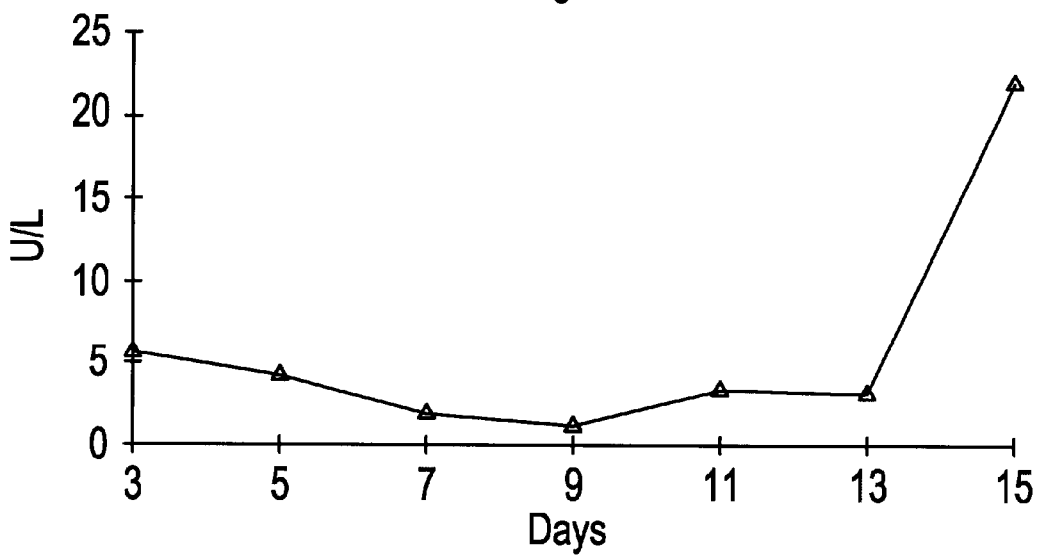
FIG. 9b. depicts production of laccase by the isolate #312 when grown in sugarcane bagasse suspended in half-strength artificial sea water.

Accordingly, FIG. 9b represents production of laccase in sugarcane bagasse medium prepared with half-strength artificial sea water by the fungus *F. flavus*, NIOCC isolate 312.

Examples 1–9 illustrate that the said fungus *Flavodon flavus*, NIOCC isolate 312, can be grown in conventional media prepared with distilled water or half-strength artificial sea water and in sugarcane bagasse suspended in distilled water or half-strength artificial sea water and the biomass of the fungus thus obtained can be used for removal of synthetic dyes in freshwater and estuarine conditions and in soil. The fungus can be immobilized using conventional methods and can be used for removal of synthetic dyes in aquatic habitats and soil. The above mentioned examples further illustrate that the degradation of synthetic dyes by the said fungus is brought about by production of lignin-modifying enzymes such as MNP, LIP and laccase in conventional media or in sugarcane bagasse medium prepared either with distilled water or half-strength artificial sea water.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated.

What is claimed is:

1. A biologically pure culture of the white rot lignin-modifying fungus *Flavodon flavus* deposited at Agricultural Research Service Culture Collection (NRRL) under accession No. 30302.

* * * * *

UNITED STATES PATENT AND TRADEMARK OFFICE
CERTIFICATE OF CORRECTION

PATENT NO. : 6,395,534 B1
DATED : May 28, 2002
INVENTOR(S) : Chandralata Raghukumar et al.

It is certified that error appears in the above-identified patent and that said Letters Patent is hereby corrected as shown below:

<u>Title page,</u>
Item [57], replace present ABSTRACT with the following:

-- [57]   ABSTRACT
The invention relates to a biologically pure culture of white rot lignin-modifying fungus *Flavodon Flavus* for removal of dyes from dye containing water or soil. The *Flavodon flavus* has been deposited at the National Institute of Oceanography, Goa, India, bearing Accession No. NIOCC #312 and has also been deposited at Agricultural Research Service Culture Collection (NRRL), 1815 North University Street, Peoria, Illinois 61604, U.S.A., bearing Accession No. NRRL 30302 on March 10, 2000. --

Signed and Sealed this

Twenty-seventh Day of May, 2003

JAMES E. ROGAN
*Director of the United States Patent and Trademark Office*